United States Patent
Goor et al.

(10) Patent No.: US 6,319,205 B1
(45) Date of Patent: *Nov. 20, 2001

(54) METHOD AND APPARATUS FOR THE NON-INVASIVE DETECTION OF MEDICAL CONDITIONS BY MONITORING PERIPHERAL ARTERIAL TONE

(75) Inventors: Daniel A Goor, Tel Aviv; Robert P Schnall, Bialik; Jacob Sheffy, Tel Aviv; Peretz Lavie, Haifa, all of (IL)

(73) Assignee: Itamar Medical (C.M.) 1997 Ltd., Caesarea (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,788
(22) PCT Filed: Jul. 23, 1997
(86) PCT No.: PCT/IL97/00249
§ 371 Date: Jan. 12, 1999
§ 102(e) Date: Jan. 12, 1999
(87) PCT Pub. No.: WO98/04182
PCT Pub. Date: Feb. 5, 1998

(30) Foreign Application Priority Data

| | | | |
|---|---|---|---|
| Jul. 30, 1996 | (IL) | | 118976 |
| Jan. 30, 1997 | (IL) | | 120108 |
| Jan. 30, 1997 | (IL) | | 120109 |
| May 21, 1997 | (IL) | | 120881 |

(51) Int. Cl.[7] .................................................. A61B 5/02
(52) U.S. Cl. ...................... 600/485; 600/481; 600/483; 600/500; 600/504; 600/507
(58) Field of Search .................. 600/485, 481, 600/490, 499, 479, 480, 454, 504, 500, 507

(56) References Cited

U.S. PATENT DOCUMENTS

| | | | |
|---|---|---|---|
| 3,104,661 | 9/1963 | Halpern | 128/2.05 |
| 3,920,004 | 11/1975 | Nakayama | 128/2.05 |

(List continued on next page.)

FOREIGN PATENT DOCUMENTS

0 465 345    1/1992  (EP) .

OTHER PUBLICATIONS

B. Hedblad, M. Ögren, L. Janzon, S.–O. Isacsson and S. E. Lindell, "Low pulse–wave amplitude during reactive leg hyperaemia: an independent, early marker for ischaemic heart disease and death. Results from the 21–year follow–up of the prospective cohort study 'Men born in 1914', Malmö, Sweden," J. Int. Med., vol. 236, pp. 161–168 (1994).

(List continued on next page.)

*Primary Examiner*—Cary O'Connor
*Assistant Examiner*—Navin Natnithithadha
(74) *Attorney, Agent, or Firm*—Sughrue, Mion, Zinn, Macpeak & Seas, PLLC

(57) ABSTRACT

A method and an apparatus for non-invasive detection of a physiological state or medical condition are disclosed. The method provides an indication of such state or condition such as myocardial ischemia or sleep apnea, by detecting the peripheral arterial tone's response to such state or condition, based on monitoring changes in peripheral arterial tone and determining that a change in the condition of the patient has occurred when a specific change in the peripheral arterial tone has been detected. A static pressure field is applied around the distal part of a digit of the subject. Peripheral arterial tone changes and related volume changes in the distal part of the digit are detected to thereby detect or monitor a physiological state or medical condition. The apparatus includes a finger probe (20), in the form of a tube (3) accommodating the patient's finger, which is designed to apply pressure, and a contiguous pressure cuff (40) which extends the boundary of the pressure field. The finger probe (2) either includes or is associated with a signal sensor/transducer (100, 101).

68 Claims, 25 Drawing Sheets

U.S. PATENT DOCUMENTS

| | | | |
|---|---|---|---|
| 4,030,485 | | 6/1977 | Warner . |
| 4,112,491 | | 9/1978 | Bugay .................................. 364/415 |
| 4,406,289 | | 9/1983 | Wesseling et al. .................. 128/670 |
| 4,437,470 | | 3/1984 | Prost .................................... 128/679 |
| 4,677,984 | * | 7/1987 | Sramek ................................ 600/481 |
| 4,821,734 | | 4/1989 | Koshino ............................... 128/680 |
| 4,836,219 | | 6/1989 | Hobson et al. . |
| 4,846,189 | | 7/1989 | Sun ...................................... 128/679 |
| 4,862,895 | | 9/1989 | Yamasawa et al. ................. 128/680 |
| 4,926,867 | | 5/1990 | Kanda et al. ........................ 128/633 |
| 5,065,749 | | 11/1991 | Hasebe et al. ...................... 128/664 |
| 5,280,791 | | 1/1994 | Lavie . |
| 5,337,744 | | 8/1994 | Branigan ............................. 128/633 |
| 5,365,924 | * | 11/1994 | Erdman ............................... 600/481 |
| 5,438,986 | | 8/1995 | Disch et al. ......................... 128/633 |
| 5,542,421 | * | 8/1996 | Erdman ............................... 600/481 |

OTHER PUBLICATIONS

Chapter 23, "Air plethysmography in arterial and venous disease," Non–Invasive Diagnostic Techniques in Vascular Disease, Third edition, E. F. Bernstein (ed.), Mosby, St. Louis (1985).

Chapter 59, "The pulse volume recorder in peripheral arterial disease," Non–Invasive Diagnostic Techniques in Vascular Disease, Third edition, E.F Bernstein (ed.), Mosby, St. Louis (1985).

C. M. Edwards, J. M. Marshall and M. Pugh, "The cutaneous vasoconstrictor response to venous stasis is normal in subjects with primary Raynaud's disease," Clin. Auton. Res.; vol. 9, No. 5, pp. 255–262 (1999).

M. Ögren, B. Hedblad, S.–O. Isacsson, L. Janzon, G. Jungquist, S.–E. Lindell and P. Wollmer, "Plethysmographic pulse wave amplitude and future leg arteriosclerosis," Atherosclerosis, vol. 113, pp. 55–62 (1995).

*British Journal of Anaesthesia*, vol. 57, No. 5, "Photo–Electric Plethysmorgraphy as a Monitoring Devices in Anaesthia," Dorlas et al, pp. 524–530 (1985).

*British Journal of Anaesthesia*, vol. 57, No. 5, "Comparison of Phethysmograms Taken from Finger and Pinna During Anesthesia," Nijoboer et al, pp. 531–534 (1985).

R.P. Schnall, N. Gavriely, S. Lewkowicz and Y. Palti, "A rapid noninvasive blood pressure measurement method for discrete value and full waveform determination", Journal of Applied Physiology, Jan. 1996, pp. 307–314.

R.P. Schnall, Abstract of Doctoral Thesis, "The Development of a New Blood Pressure Measurement Technique and its Application to the Study of the Circulation", Abstracts of Research Theses, Sep. 1991, p. 68.

R.P. Schnall, Research Thesis, "The Development of a New Blood Pressure Measurement Technique and its Application to the Study of the Circulation", Sep. 14, 1990.

C. Guilleminault, R. Stoohs, A. Clerk, M Cetel and P. Maistros, "A Cause of Excessive Daytime Sleepiness. The Upper Airway Resistance Syndrome", Chest 104, pp. 781–787 (1993).

P. L. Ludmer, A. P. Selwyn, T. L. Shook, et al., "Paradoxical Vasoconstriction Induced by Acetylcholine in Atherosclerotic Coronary Arteries", New England Journal of Medicine, vol. 315, No. 17, pp. 1046–1051 (1986).

L. Kuo, M. J. Davis and W. M. Chilian, "Endothelium–Dependent, Flow–Induced Dilation of Isolated Coronary Arterioles", The American Physiological Society, vol. 259, pp. H1063–H1070 (1990).

D. Jain, M. Burg, R. Soufer and B. L. Zaret, "Prognostic Implications of Mental Stress–Induced Silent Left Ventricular Dysfunction in Patients with Stable Angina Pectoris", The American Journal of Cardiology, vol. 76, pp. 31–35 (1995).

W. Jiang, M. Babyak, D. S. Krantz, R. A. Waugh, R. E. Coleman, M. M. Hanson, et al., "Mental Stress–Induced Myocardial Ischemia and Cardiac Events", JAMA, vol. 275, No. 21, pp. 1651–1656 (1996).

A. Rozanski, J. A. Blumenthal and J. Kaplan, "Impact of Psychological Factors of the Pathogenesis of Cardiovascular Disease and Implications for Therapy", Circulation, pp. 2192–2217 (1999).

C. Kurata, K. Tawarahara, K. Sakata, T. Taguchi, Y. Fukumoto, A. Kobayashi, et al., "Electrocardiographically and Symptomatically Silent Myocardial Ischemia During Exercise Testing", Japanese Circulation Journal, vol. 55, pp. 825–834 (1991).

M. Ishibashi, T. Yasuda, N. Tamaki and H. W. Strauss, "Evaluation of Symptomatic vs. Silent Myocardial Ischemia Using the Ambulatory Left Ventricular Function Monitor (VEST)", Israel Journal of Medical Science, vol. 25, No. 9, pp. 532–538 (1989).

\* cited by examiner

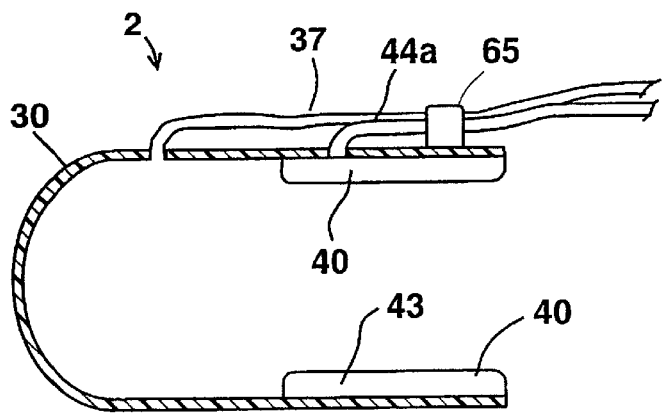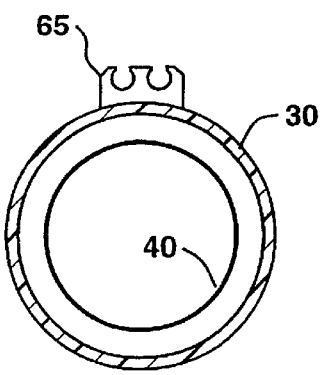
FIG. 6a　　　　　　　　FIG. 6d
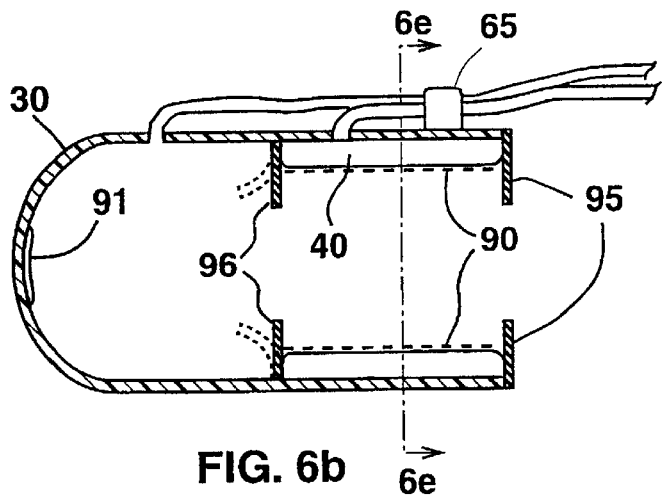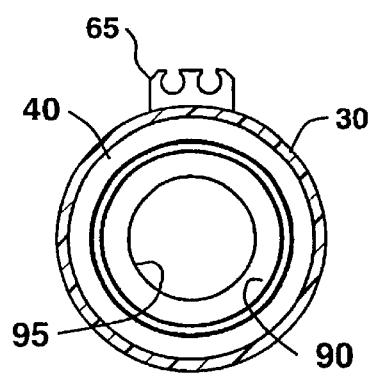
FIG. 6b　　　　　　　　FIG. 6e
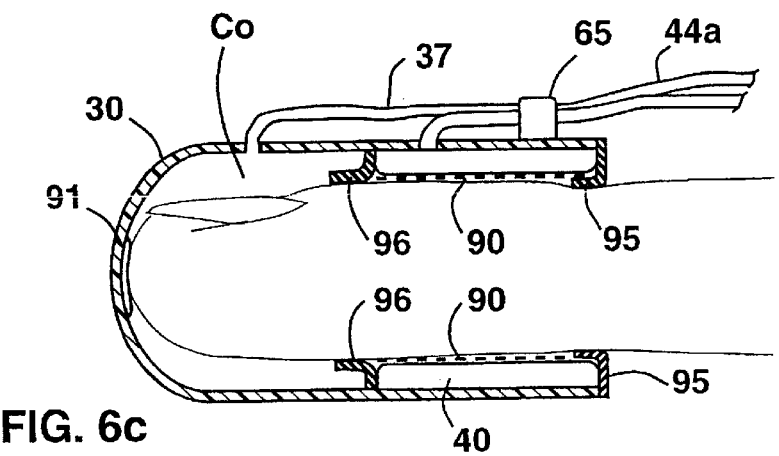
FIG. 6c

IschemoGraph Vs. Thallium Spect

|  | Positive<br>Thallium Spect<br>(53) | Negative<br>Thallium Spect<br>(40) |
|---|---|---|
| Positive IschemoGraph | 53 | 12 |
| Negative IschemoGraph | 0 | 28 |

IschemoGraph consistent with Thallium 81/93=87%
12 unconfirmed positive compared with Thallium

FIG. 14

Results of 93 stress tests performed at Sheba Medical Center and Kaplan Hospital Thallium IschemoGraph Legend:
0 - Increase grade
2 - Thallium injection
3 - Stop Thallium IschemoGraph Legend:
0 - Increase grade
2 - Thallium injection
3 - Stop

ECG Vs. Thallium Spect

|  | Positive Thallium Spect (53) | Negative Thallium Spect. (40) |
|---|---|---|
| Positive ECG | 20/53 (38%) | 7/40 (17.5%) |
| Ambiguous ECG | 11/53 (21%) | 6/40 (15%) |
| Negative ECG | 22/53 (41%) | 27/40 (67.5%) |

ECG false negative:     22-33 (41%-62%)

ECG consistent with Thallium 47/93 (50%)

FIG.17

Results of 93 stress tests performed at Sheba Medical Center and Kaplan Hospital

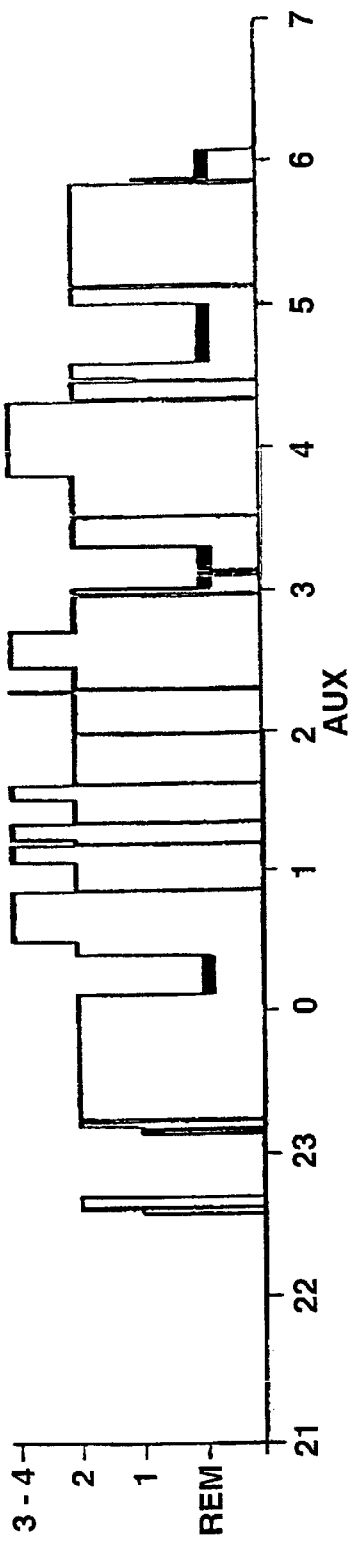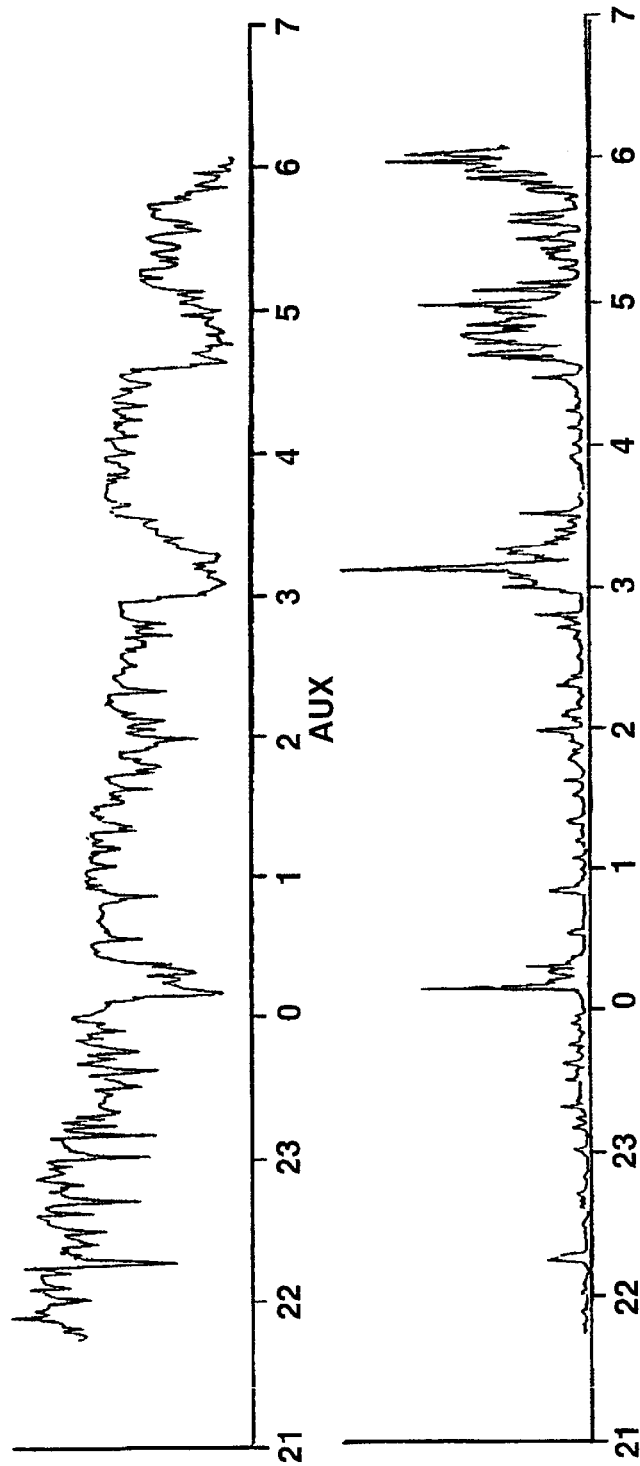
FIG. 21a RAPID EYE MOVEMENT (REM) MONITOR
FIG. 21b
FIG. 21c

METHOD AND APPARATUS FOR THE NON-INVASIVE DETECTION OF MEDICAL CONDITIONS BY MONITORING PERIPHERAL ARTERIAL TONE

BACKGROUND OF THE INVENTION

1. Field of the Invention

The present invention relates to a method and apparatus for the non-invasive detection and monitoring of a physiological state or medical condition by monitoring peripheral arterial tone. More specifically, the present invention relates to monitoring changes in the peripheral arterial vasoconstriction in reaction to such state or condition, particularly those related to cardiopulmonary distress and blood pressure in order to detect or monitor the physiological state or medical condition of the patient.

2. Description of Related Art

As noted above, the present invention relates to detection and monitoring of various physiological states and medical conditions by detecting hemodynamic events in body extremity of the patient. However, while the present invention relates to detecting and monitoring numerous physiological states and medical conditions, four particular examples generally related to cardiopulmonary distress and blood pressure are provided herein; namely, myocardial ischemia, sleep staging, sleep apnea syndrome, and continuous blood pressure monitoring. Therefore, the following discussion includes description of art related to these four examples.

Definitions of Related Terms in Myocardial Ischemia

1. Ischemia - a term used when an organ in the body is inadequately perfused with blood.

2. Myocardial ischemia - a term used when the heart muscle—myocardium—is ischemic.

3. Angina pectoris - (cardiac pain) - the clinical symptomatology usually produced by myocardial ischemia. Classically, these symptoms consist of pain, or discomfort, or pressure felt in the chest and/or in the left arm.

4. Atypical angina pectoris - ischemic events may produce atypical symptomatology, such as pain in the neck, molar teeth, and in other places.

5. Silent angina pectoris - refers to the condition of asymptomatic (painless) myocardial ischemia.

Silent angina is present in approximately 20% of people who sustain ischemic episodes. Consequently, they do not realize they have a life-threatening problem, and they do not seek medical advice. They are therefore at risk of sudden and unexpected death.

6. Coronary artery disease - the coronary arteries are the vessels which nourish the heart. In arteriosclerosis, narrowing inside the coronaries is caused by the swelling of voluminous cholesterol and calcium debris, replacing the normal elements of the walls of the arteries.

7. Chronic angina pectoris - in this category of angina pectoris, the ischemic symptoms are related to physical effort (i.e. are "demand-related"). The increased demand for blood required by the laboring heart cannot be accommodated by the fixed, non-expandable, rigid arteriosclerotic narrowing.

8. Unstable angina pectoris - in this category of angina pectoris, a clot of blood forms spontaneously in an arteriosclerotic narrow segment suddenly and unexpectedly, partially obstructing the artery and inducing myocardial ischemia. In most instances the clot is spontaneously dissolved after a while, the blood perfusion is reinstituted, and the myocardial ischemia is relieved.

9. Myocardial infarct - When the forming clot is not dissolved, but rather progresses to the state of a totally obstructing thrombus, or when atheroma ruptures blocking the artery, the myocardium, which is nourished by the involved artery, succumbs to necrosis. That is the myocardial infarct.

10. Arterial tone - The degree of "active tension" which the smooth muscle fibers surrounding the arteries impart. When activated (usually by sympathetic nerve endings or by blood bourne or locally elaborated mediators), these fibers contract and in so doing reduce the calibre of the arteries. When the degree of active tension is high, this results in state of vasoconstriction and conversely, when the degree of active tension is low vasodilation occurs. Apart from active tension, arterial walls also experience passive tension which is due to the blood pressure within the arteries.

11. Coronary angiography - The practice of the radiographic visualization of the coronary arteries. A radioopaque material is injected into the origin of the coronary arteries within the aorta by way of an arterial catheter which is inserted into an artery of an arm or leg, and is then advanced through the artery towards the heart.

12. Cardiopulmonary distress - a general term used to describe a low grade negative impact on the patient induced by an acute impairment in the cardiopulmonary function. This can result from, among others, myocardial ischemia, valvular heart disease, cardiomyopathy, congestive heart failure and chronic lung disease.

Prior Art Methods for Detecting Myocardial Ischemia

In patients who sustain typical episodes of unstable angina pectoris associated with pain, the diagnosis of spontaneous ischemia is made on the basis of their symptoms. Usually, coronary angiography is performed on these patients for selecting the mode of therapy (e.g. surgery, drug therapy, balloon angioplasty, etc.). However, people who complain about chest pain linked to physical activity, as well as people in whom, for other medical reasons, the presence or absence of coronary artery disease needs to be determined, are referred to cardiac stress tests.

In cardiac stress tests the heart is provoked to increase its demand for oxygen by using treadmill, bicycle and other physical stress exercises, or pharmacologically. A number of methods, as described herein, are available for detecting events once a demand related ischemia develops during cardiac stress tests. The predictive values of such existing methods, however, vary from approximately 50% to 85% and therefore none is sufficiently reliable to be used as a sole determinate of disease or a universal standard.

The following are the diagnostic techniques in use for detecting myocardial ischemia elaborated during exercise tests:

1) ECG (Electrocardiography): The ECG depicts abnormal electrical activities which may arise in ischemic myocardial regions. The sensitivity and specificity of the ECG in detecting myocardial ischemia is directly related to the extensiveness of the arteriosclerotic disease. Hence, high risk localized disease (i.e. limited to one or two arterial branches) may be easily overlooked. Although the overall predictive value of ECG in stress test is only approximately 60%, it is still the most important tool for detecting chronic angina pectoris, and because of its easy applicability and low cost, it is the only available method for screening purposes.

2) Stress echocardiography: This technique is based on two dimensional ultrasonic imaging of the walls of the heart. During the stress testing the myocardial segments related to arteriosclerotic coronary arteries may become ischemic. Consequently, wall motion disturbances, such as hypokinesia and/or a decrease in wall thickening, may be depicted by the echocardiograph. Continuing improvements in this technique have increased the predictive diagnostic value of stress echo to approximately 75%–80%, which is nearly as high as nuclear imaging technologies. The test can be performed in the doctor's office but since it is labor intensive and professionally demanding it is not appropriate for mass screening.

3) Nuclear imaging technologies. In each of the nuclear technologies described below, radioactive isotopes are injected intravenously. In techniques b and c described below, a second intravenous dose of the same isotope is required some time after the first is washed out and the patient is at rest. This enables the physician to distinguish between filling defects due to infarcted regions versus transient filling defects in demand-related ischemic segments.

Patients deemed to have a significant degree of demand related myocardial ischemia on the basis of the diagnostic tests described below are usually then referred for cardiac catheterization and coronary angiography, which is the most invasive, but also the most definitive diagnostic test available. In most cases the ultimate treatment choice in cases in which nuclear tests are positive, is determined by such angiography. In certain circumstances, however, patients found to have diffuse coronary disease during angiography will be referred back to one of the nuclear diagnostic techniques to determine the functional effects of the anatomical defect.

a. MUGA (Multigated Angiography). In this method, the injected labeled technetium (Tc) is taken up by the red blood cells. Cineangiography of the cavity of the heart which is filled with the labeled blood can reflect ischemic wall motion disturbances. Reliability of this test is approximately 80–83%.

b. 201-Thallium (Tl) planar scanning. The injected 201-Tl is a radioactive tracer which is "absorbed" by the viable myocardial cells. In infarcted or inadequately perfused ischemic regions, Thallium uptake by the myocard is stopped, and appears in planar scanning pictures as filling defects. Reliability is approximately 80–83%.

c. Thallium SPECT (Single Photon Emission Computed Tomography). This is a more advanced technology in Thallium imaging than the planar scanning. With this technology a distinction between filling defects due to infarct versus temporary ischemia can be made. In a second scanning performed a few hours after the first one, uptake of the radioactive tracer can be seen in previously ischemic regions. Once the demand-related relative perfusion insufficiency is gone and the perfusion reinstituted, the circulating Thallium can reach and be traced in the reperfused myocardium. At the present time, this method is the conventional standard in clinical routines for ischemia detection for use after a positive result was obtained with ECG, or based on the physician's assessment of the patient. Reliability is in the range of 82–85%.

d. PET (Positron Emission Tomography). In this method, metabolic activity is traced by radioactive labeled agents that ordinarily participate in the cycles of metabolism, like glucose. Metabolism is the sign of life, and as such, a guide for viability of the myocardium. In addition, PET can be used for perfusion studies.

While the PET scan methodology is the most accurate of the nuclear tests it is extremely expensive (multi-million dollar equipment and specialized facilities) and, as with the other nuclear tests, patients testing positive are ultimately referred to angiography for a definitive therapeutic decision.

Notably, all the above techniques are designed to detect impairments in various functions of the ischemic heart. That is, the prior art methods monitor or detect the functioning or dysfunctioning of the heart itself due to the continuing presence of ischemia. On the other hand, as will be described more fully below, the present invention monitors the response of the peripheral arterial tone to the onset of myocardial ischemia.

Generally, two functions participate in maintaining the blood pressure (BP) at the physiologically desired level: 1) Cardiac output (CO), measured in liters per minute; and 2) systemic (in contrast to pulmonary) vascular resistance, (SVR), measured in dynes/sec/cm$^5$. The term systemic vascular resistance refers to the impedance to the blood flow in the systemic arterial vascular bed, and it is regulated by the arterial tone.

The relationships of blood pressure, cardiac output (CO), and SVR are grossly expressed in the formula BP=CO×SVR, and conventional techniques for determining the SVR involve measuring the blood pressure and CO and calculating therefrom the SVR. However, a co-inventor of the present invention (Goor) has previously proposed to measure the SVR directly. See, U.S. Pat. Nos. 4,429,701, 4,798, 211, and 4,821,735, all to Goor et al. and all incorporated herein by reference. In U.S. Pat. No. 4,429,701, a novel method and apparatus—the Resistometer—are disclosed for direct monitoring of changes in SVR. Subsequently, in U.S. Pat. No. 4,798,211, it was disclosed that when using the Resistometer for monitoring the SVR during percutaneous transluminal coronary angioplasty (PTCA), each time the balloon was inflated, totally obstructing the involved coronary artery, a rise in SVR followed (See, Mohr et al, Circulation 74:780–6, 1986).

Nevertheless, the method and apparatus disclosed in the above patents to Goor et al. relied on measuring SVR directly and required invasive techniques to do so. More specifically, the SVR was measured directly by a needle placed in the femoral artery. Moreover, although it was postulated that the SVR may be monitored non-invasively, to date no non-invasive method or apparatus for direct monitoring of SVR is available.

Peripheral vasoregulation is a well known physiological phenomenon. It is known, for example, that the body normally regulates is temperature by changing the blood flow to the skin so as to regulate the body's temperature via heat exchange. Thus, vasodilation brings warm blood to the skin to increase heat radiation to the environment, while vasoconstriction reduces the amount of blood flow to the skin to conserve heat. Peripheral vasoconstriction also occurs during traumatic bleeding or internal bleeding to ensure a stable blood pressure and blood supply to the brain, liver, kidneys, and other vital organs. Vasoregulation in the body by means of vasoconstriction and vasodilation is a very sensitive mechanism, which is controlled by the brain as well as by local mediators, and is constantly regulated to maintain optimal perfusion of the body organs in physiological and pathological conditions.

The incidence of myocardial ischemia and related risk of death in Western societies can be estimated on the basis of the following estimated data for Israel. There are approximately five million people in Israel. Of these, an estimated 250,000 are cardiac patients, 80–85% of whom have coronary artery disease. Of these patients with known coronary artery disease approximately 80–90% have chronic angina pectoris. Mortality in this group of treated patients is approximately 1–2% a year. The remaining 10–20% suffers from the unstable form of angina pectoris. In this group of treated patients, annual mortality figures can reach 10–20%.

It is estimated by Israeli experts that in addition to the estimated 250,000 cardiac patients, approximately the same number of people have cardiac disorders that are undiagnosed. This estimate is supported by the fact that of approximately 6,000 cardiac deaths per annum in Israel, half were totally unexpected, occurring in people not considered to be cardiac patients. Therefore a well-known, major health-care problem exists in Western societies since an estimated 10–20% of persons with coronary artery disease, and who therefore are subject to all forms of myocardial ischemia, have no pain or other symptoms of this disease.

Accordingly, there is a critical need for a simple, inexpensive, non-invasive technique for detection of myocardial ischemia resulting from the presence of coronary artery disease, which is more predictive than the currently available stress ECG tests.

Art Relating to Sleep Conditions and Sleep Apnea

Normal individuals experience several distinct sleep stages. One important sleep stage, known as REM sleep, is characterized by rapid eye movement, small muscle twitches, changes in autonomic activity, and the absence of other body movements. The other sleep stages, known as Non-REM (NREM) sleep, are subdivided into four stages, wherein the first stage is the most shallow, i.e., the least restful or refreshing, and the fourth stage is the deepest.

Monitoring an individual's REM sleep is very important for diagnosing sleep disorders. It also is useful in various fields, such as therapy, diagnosing and following response to treatment of depression and narcolepsy in which REM latency is significantly reduced, and in research.

For diagnosis, the patient's sleep should be monitored to determine the pattern and duration of various sleep stages. Sleep is qualitatively and quantitatively evaluated by measuring electrical signals produced by brain and muscle activity, using electrophysiological techniques and electronic instruments.

A widely used technique for this purpose involves a simultaneous and continuous measuring of electroencephalographic (EEG) data. EEG data are signals derived primarily from the cortex of the brain, and also are referred to as electrocardiogram (ECoG). At the same time an electromyogram (EMG) signal which monitors muscle activity, generally from one of the muscles of the lower jaw, is measured together with left eye and right eye electro-oculogram (EOG) signals produced by eye movements. These EEG, EMG, and EOG signals are conventionally recorded on a multi-channel physiological recorder.

Photographic techniques also have been used to evaluate sleep state. According to Hobson et al (Science 201, 1978, p. 1251–5), the mobility of a sleeping subject is measured photographically and the predicted transitions between NREM and REM are done on the premises that major body posture shifts occur immediately preceding and following REM sleep.

According to U.S. Pat. No. 4,784,162 an apparatus is described for monitoring sleep disorders using a plurality of sensors adapted for attachment to the patient. The sensors generate analog signals which are subsequently converted to binary data to be transmitted by low-power radio. According to U.S. Pat. No. 4,836,219, a method and device are described for reporting an individual's sleep state using electronic filters applied to analog signals representative of eye movements and head movements from detectors attached to a headgear.

U.S. Pat. No. 5,280,791, to co-inventor Lavie, relates to a system for determining the sleep state of a person, which comprises: (a) means for measuring the person's cardiac R—R waves interval; (b) means for calculating the power spectrum of the cardiac R—R interval thus obtaining a ratio between spectral power in slow and high frequencies; (c) means responsive to the measuring and the calculating means for generating output signals, one output signal having a first value when designated as REM sleep, and one output signal having a second value when the above ratio is below this threshold designated as NREM sleep; and (d) means responsive to the output signal for designating a time period of predetermined duration as a REM period or a non-REM period respectively. The preferred spectral power is generally in the range of between 0.01 to 0.07 Hz for the slow frequency and between 0.2 to 0.3 Hz for the high frequency.

Sleep apnea syndrome is one of the most common and serious sleep disorders. It is characterized by repetitive episodes of upper airway collapse during sleep resulting in interruption of airflow despite persistent respiratory effort. Obstructive apneas are typically associated with progressively increasing asphyxia until termination by a brief arousal from sleep and restoration of upper airway patency. Population studies (from the inventors' laboratory and by others) have estimated that 2–4% of the adult population suffer from sleep apnea syndrome. The syndrome has been identified as an important risk factor to systemic hypertension, myocardial infarction, stroke, and sudden death. To diagnose sleep apnea syndrome, usually simultaneous recordings are made on a multi-channel recorder consisting of an electroencephalogram (EEG), electro-oculogram (EOG), submental electromyogram (EMG), oro-nasal airflow (by thermistors or thermocouples) and thoraco-abdominal movements (by respiratory belt), snoring intensity (by dB meter), pulse oximetry and leg movements. Each record is scored visually for all apneic events. The recordings are cumbersome and may interfere with patients' sleep.

In view of the difficulties with existing sleep evaluation techniques, there are many cases in which only partial monitoring is conducted, consisting only of respiratory effort and oximetry. Partial recordings are done particularly for screening purposes. Their purpose is to identify persons with large numbers of apneic events.

Accordingly, there is a need for a simpler method for sleep staging and sleep apnea syndrome detection, which would allow the patient to sleep comfortably during the evaluation.

Background Information Related to Blood Pressure

Many diagnostic and treatment procedures require an accurate and consistent monitoring of blood pressure, especially the systemic arterial systolic and diastolic blood pressure. It often would also be desirable to obtain the mean blood pressure and the shape of the pulse wave. Prior art methods and apparatuses for monitoring blood pressure can generally be classified as either non-invasive or invasive. The non-invasive methods are used when periodic individual measurements of arterial systolic and diastolic blood pressure data are sufficient. Invasive methods are used when reliable continuous monitoring of the blood pressure is needed, or when the shape of the pulse wave is required. The conventional method of continuous blood pressure measurement involves the introduction of an intra-arterial cannula which transmits the intra-arterial pressure waveform to a pressure measuring apparatus. Due to its invasiveness, presently continuous monitoring is confined to the limited environments of critical care and operating rooms. However, there are many other situations in which it would be desirable to have continuous blood pressure monitoring, if an easy to use, reliable non-invasive method for continuous monitoring was available.

The most common methods for non-invasively measuring the blood pressure are the auscultatory and oscillometric sphygmomanometric methods, according to which a cuff is placed on the upper arm and is inflated until the artery is completely occluded. A sound detecting device is then used to detect the pulse signals during occlusion and upon reduction in the cuff's pressure. As is widely known, these methods provide only the systolic and diastolic blood pressure values, and are not suitable for continuous blood pressure measurements. Another major disadvantage of these methods is that they completely occlude an artery, thereby interfering with the normal blood flow. These methods are also known to be prone to inaccuracy, especially in people who are obese or who suffer from hardening of the arteries; are unsuitable for use on sleeping patients since the measurement process is likely to awaken the patient; and are very inconvenient to use during exercise. In addition, such methods provide infrequent data and poor resolution of blood pressure lability.

One prior art method for continuous monitoring of blood pressure is the tonometric method, which is based on measuring the form of an externally recorded pulse wave. That is, a device is used to exert a given amount of force upon a peripheral artery, while the pulsatile amplitude changes of the artery are monitored. The main drawback of this prior art technique is that it cannot be used for sustained accurate measurement and for long term accurate blood pressure measurements. Specifically, this method is sensitive to the mechanical effects of the patient's motion, limiting its effectiveness.

Another major problem with this method is the lack of accurate means for converting the force signal into a pressure signal. Specifically, at least the following two reasons prevent derivation of a universally applicable conversion factor. First, the transmission of the pulse wave to the outside of the body varies greatly from person to person. Second, the force/pressure relationship may be non-linear, thus a single set of independently measured sphygmomanometric systolic and diastolic pressure values is insufficient for proper calibration.

Another prior art method for continuous monitoring is known as the method of Penaz. This method teaches balancing the internal blood pressure in the patient's finger, while continuously changing external counter pressure to maintain a constant level of optical density in the finger, to thereby monitor the blood pressure changes. Notably, the method depends on the undesirable continuous application of substantial levels of external pressure near the intraarterial pressure level. This method is also sensitive to patient movement. The present inventors believe that, at least one cause of the method's inaccuracy is that the constant application of relatively high pressure alters venous return at the measuring site, and causes venous congestion in the part of the finger distal to the measurement site, possibly causing hemodynamic and reflex vascular changes that could result in alterations in the blood pressure measurement.

Yet another prior art method utilizes a photoplethysmograph consisting of a light transmitter and receiver placed on opposite sides of the finger tip. The receiver records the changing transmission of light through the finger, due to the changing amount of blood flowing through the artery. The received signal is transmitted to a computer for converting the receiver output into diastolic and systolic pressure data. One notable drawback of this method is that it lacks accurate means of calibration for converting the changing light output into blood pressure. Also the influence of venous blood within the finger is indeterminate and may have substantial deleterious effects as described later.

Accordingly, there is a need for a simple, non-invasive technique for continuous blood pressure monitoring.

SUMMARY OF THE INVENTION

As will also be described more fully below, the present inventors have determined that a physiological state or medical condition can be determined by detecting characteristic hemodynamic events in the body extremity of the patient. Specifically, the present inventors have demonstrated that cardiopulmonary distress, can be detected and monitored not only by measuring rising SVR, but rather by directly measuring the evolution of peripheral vasoconstriction. This enables detection using a non-invasive method which is very simple and inexpensive to implement.

Accordingly, an object of the present invention is to provide a non-invasive method and apparatus enabling accurate and consistent detection of a physiological state or medical condition by detecting changes in the peripheral arterial tone in reaction to certain eliciting effects.

A more specific object of the present invention is to provide a method and an apparatus for the detection of cardiopulmonary distress, by detecting and monitoring peripheral vasoconstriction.

While it has been known that the arterial tone is a mechanism used by the body to control various functioning parameters, the present inventors have demonstrated that changes in the arterial tone can also be used as a valuable diagnostic tool for physiological dysfunction or medical condition. More specifically, the present inventors have demonstrated that one may detect physiological dysfunction, such as myocardial ischemia, by directly measuring peripheral vasoconstriction, which is an initial factor leading to the rise in SVR discovered previously and reported in the above cited patents to Goor et al.

Accordingly, disclosed herein is a method and apparatus for the non-invasive monitoring of peripheral arterial tone. While changes in the peripheral arterial tone may be detected by monitoring changes in any of a number of hemodynamic parameters such as blood flow, blood volume, and the shape of the arterial pulse wave, of any peripheral arteries, such as in the patient's skin, it is preferably conducted on the patient's finger or toe, to detect changes in the pulsatile volume of arterial blood of such location. The changes in the amount of blood can be determined by plethysmography of one or more parameters, such as the finger's volume, optical density etc. The finger is an advantageous site because of its easy access, but other regions of the body extremity could also be used.

In its preferable construction, the apparatus of the present invention comprises a finger probe that receives all or a portion including the distal end of the patient's finger. The finger probe includes a non-flexible thimble shaped outer shell and a compliant membrane substantially in the shape of a latex glove finger. A cylindrical pressure band divides the membrane into two parts, generally constituting a bladder and a pressure cuff. A U-shaped metal bar divides the bladder into two communicable compartments. These two compartments are applied to the distal part of the finger and then pressurized. The pressure cuff is pressurized separately from the bladder compartments. In the preferred embodiment, the pressure should be sufficient to prevent blood pooling in the veins at the measuring site, and to unload the tension in the arterial walls. However, the applied pressure should not be raised so high as to occlude the arteries. The finger probe may include means for detecting the changes in the arterial tone, such as pressure transducers or photoelectric cells. Alternatively, the finger probe may include conduits to transmit the sensed information to sensors positioned externally to the probe.

Notably, the method and apparatus according to the invention is suitable for detecting and monitoring various physiological states and medical conditions, in addition to myocardial ischemia. For example, the present inventors have demonstrated that the method and apparatus of the invention are suitable for two important areas in sleep monitoring: Rapid Eye Movement (REM) sleep staging, and sleep apnea syndrome.

Additionally, the present inventors have demonstrated that the inventive apparatus can be used for mass screening of population during sleep to detect silent or overt nocturnal angina pectoris. This cannot be presently done since all prior art methods are cumbersome and may interfere with the patient's sleep. In addition all present methods involve substantial equipment and are very expensive and, therefore, inappropriate for mass screening.

With certain modifications and a novel calibration procedure, the present invention has been demonstrated to be useful for continuous non-invasive measurement of blood pressure.

BRIEF DESCRIPTION OF THE DRAWINGS

The invention is herein described, by way of example only, with reference to the accompanying drawings, wherein:

FIG. 3b is a cross-sectional view along line A'—A' of FIG. 3a;

FIG. 4a illustrates the probe of FIGS. 2a and 2b, while

FIGS. 6 illustrates yet another embodiment of the pressure cuff according to the present invention;

FIGS. 6a–6e illustrate embodiments wherein the pressure cuff is used to allow measurements without the need for the bladder;

FIGS. 12–20 set forth graphical data illustrating the results produced by the present invention when used for detecting myocardial ischemia, and also comparative data comparing these results with known techniques for detecting myocardial ischemia;

FIGS. 21 and 22 set forth graphical data illustrating the results produced by the present invention when used for monitoring a sleeping condition of a subject, particularly for detecting REM (rapid eye movement) stages and sleep apnea;

DETAILED DESCRIPTION OF THE PREFERRED EMBODIMENTS

Detection of Myocardial Ischneia

Figure 1:
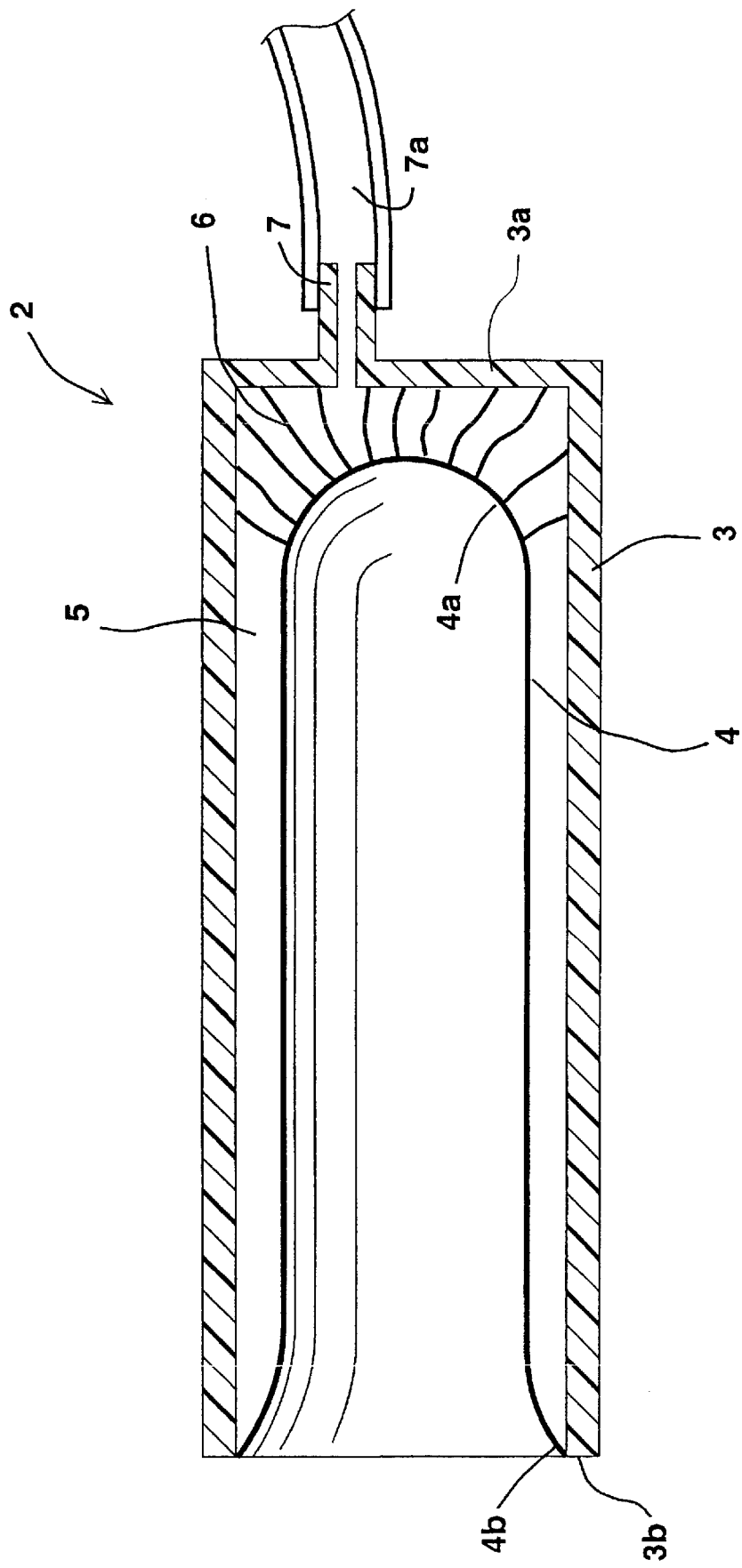
FIG. 1 is a sectional view diagrammatically illustrating one embodiment of the inventive probe to be applied to the subject's digit (e.g., finger) for monitoring the peripheral arterial tone of the subject.

A particularly important advantage of the present invention is the ability to non-invasively detect the existence of cardiopulmonary distress, especially myocardial ischemia. Therefore, the following discussions and explanations of the inventive method and apparatus relate mainly to detecting myocardial ischemia. However, it should be appreciated that the present invention can be used to detect other physiological states and medical conditions for which the body's reaction is reflected in the peripheral arterial tone. Some examples will be provided following the discussion of myocardial ischemia.

In order to more fully convey the advantageous features of the method and apparatus of the present invention, a short explanation of a few physiological reactions to spontaneous (unstable) myocardial ischemia is provided herein. Historically there were at least two views regarding onset of this type of myocardial ischemia. According to Gorlin (Circulation 32:138, 1965), it is a sudden rise in the blood pressure that induces an increased burden on the heart, accounting for the development of demand related ischemia. According to Chierchia (Circulation 61:759, 1980), spontaneous onset of ischemia is a primary event, and when certain cardiopulmonary functional changes (such as heart rate, blood pressure, ECG changes, etc.) are present they are caused by the myocardial ischemia.

Data obtained by the present inventors, using the inventive apparatus (referred to by the inventors as the Ischemograph), indicate that once ischemia is induced such as by inflating the balloon during PTCA, peripheral vasoconstriction becomes apparent within 10–20 seconds. (Previously it was shown by the present inventors using the Resistometer that a rising SVR can also be detected under these circumstances.) Also, during echocardiographic exercise tests monitored by the inventive apparatus, it was learned that peripheral vasoconstriction occurs before any signs of deterioration in cardiac contractility are displayed.

At this state of knowledge, the present inventors can offer a few possible explanations for the rapid influence of the evolving myocardial ischemia on the peripheral arterial tone. The first is by means of a direct stimulation of the peripheral arterial tone by reactive sympathetic activity. Another possible explanation is by a local mediation of the vascular tone by factors such as thromboxane released into the circulation from the ischemic myocardium (see, Teoh, J. Thorac Cardiovasc Surg. 93:120, 1987). A further explanation is by local mediation of the vascular tone by one or more of the endothelial borne agents, such as endothelin-1.

Hence, once myocardial ischemia has begun, its progression can be devastating to the patient. The reactive peripheral vasoconstriction results in a rise of SVR with a related increase in blood pressure. The high blood pressure increases the demand related ischemia as described by Gorlin, leading to diastolic dysfunction followed by systolic dysfunction of the left ventricle, leading to a decrease in cardiac output, which in turn further disrupts the equilibrium of the SVR formula, further aggravating the peripheral vasoconstriction, with the end results depending on the duration of ischemia and the size of the inflicted muscle.

According to the present invention, the onset of myocardial ischemia can be detected by directly measuring changes in peripheral vasoconstriction. The present inventors also determined that the peripheral vasoconstriction can be measured by detecting changes in peripheral arterial intravascular volume. For example, the magnitude of the arterial pulse wave in a single digit of the patient can be monitored. Thus, a drop in the magnitude of the arterial pulse wave in such digit, would indicate a drop in the arterial blood volume in such digit indicating the presence of peripheral vasoconstriction, and therefore an increase in peripheral resistance, which in turn would suggest an increase in SVR.

The term SVR refers to the lumped resistance to blood flow of all the systemic blood vessels and is determined as the ratio of blood pressure, (actually arterial minus venous pressure), to cardiac output. The calculated SVR gives the overall summation of all the resistance of the entire systemic circulation at the point of blood ejection from the heart.

The term peripheral resistance (PR), on the other hand, refers to the resistance in the body extremities, such as the skin or other body surface, or a digit, such as a finger or a toe. Under certain circumstances, peripheral resistance could behave quite differently than SVR, for example a man doing heavy work in a very cold environment would have a relatively high peripheral resistance value of the skin but resistance to flow in active muscles could be low. Consequently, while a rising SVR is ordinarily associated with a rising peripheral vasoconstriction, direct measurement of peripheral vasoconstriction would probably be a more sensitive parameter than SVR in detecting myocardial ischemia. In addition, SVR can also change with changes in cardiac output.

The inventive apparatus allows monitoring of pulsatile volume changes in the arterial vasculature of the finger, and was demonstrated to be efficient in detecting peripheral vasoconstriction. In extreme conditions of vasoconstriction, the peak to trough size (amplitude) of the pulse waves picked up by the apparatus may decline to an almost straight line, indicating the body's response to a physiological event. When used for monitoring the peripheral response to the balloon inflation of major coronary arteries during PTCA, particularly when nitroglycerin is not administered to the patient, the apparatus identifies unequivocal reduction in blood volume in the measured arterial vasculature, an indication of increased arterial tone and peripheral vasoconstriction.

Hence, the inventive apparatus directly detects the morphological change in the peripheral circulation that partially underlies the change in SVR identified by the Resistometer disclosed in the above patents to Goor et al. when myocardial ischemia is present. Furthermore, while the Resistometer invasively measures SVR, the device of the present invention noninvasively directly measures peripheral vasoconstriction.

Preferred embodiments of the Apparatus

The inventive apparatus generally comprises a novel finger probe and a processing system for controlling the measurement process and collecting and processing the signals of the finger probe. The following includes a description of several embodiments of the finger probe and the processing system, including the preferred embodiments thereof.

The Finger Probe

FIG. 1 illustrates a finger probe 2 constructed according to an embodiment of the present invention. Finger probe 2 includes a rigid tubular casing 3 of a diameter somewhat larger than a person's finger. Casing 3 is closed at one end by an end wall 3a and is open at the opposite end 3b for receiving the person's finger. A deformable membrane (or bladder) 4 of tubular configuration is located within casing 3 and is similarly closed at one end 4a and open at the opposite end 4b. Tubular membrane 4 may be of an elastomeric material, or of a thin, pliable plastic sheet material, and is generally similar to a finger of a latex glove. It is of a diameter to define a socket for receiving the end of the finger and to produce between the membrane and the inner surface of casing 3 a closed tubular chamber 5 which expands and contracts depending on the pressure inside chamber 5.

The open end 4b of tubular membrane 4 is hermetically secured to the open end 3b of the casing 3. The closed end 4a of the tubular membrane may be yieldingly secured to the closed end 3a of the casing by any suitable manner, to prevent axial movement of the tubular membrane outwardly of the casing but not inwardly of the casing. In FIG. 1a this is exemplified by a plurality of flexible, non-stretchable strings 6 which prevent axial movement of the tubular membrane outwardly of the casing but not inwardly of the casing. However, other suitable means may be used to achieve the same effect, and further examples will be provided below.

Chamber 5, between the casing 3 and the tubular membrane 4, is connected to a source of compressed air or other fluid via a port 7 formed in the casing end wall 3a, and a tube 7a is connected to port 7. In order to obtain measurement of the arterial blood volume, finger probe 2 is applied to the distal end of a digit, namely a finger of the subject's hand (or toe of the subject's foot), and a static pressure field is applied around the distal end of the digit.

As mentioned before, prevention of venous pooling is a notable feature of the present invention. The present inventors have determined that under normal circumstances, venous blood is arbitrarily and unpredictably shifted and pooled in the finger's pulp. Therefore, any attempt to measure volume/pressure changes will be affected by the signals generated by the venous pooling, which may override and/or offset the desired signals generated by the arterial pressure waves, seriously distorting the actual measurements. An important factor in venous pooling, and one which has been essentially overlooked in the prior art, is the effect of venous shock waves. During exercise stress tests, for example, the physical activity shakes the low pressured vena cavas (the large veins conveying blood to the right atrium), generating shock waves which propagate all the way back to the fingertips.

Another cause of digital venous pooling is linked to a rise in the hydrostatic pressure in the venous column of blood. As a result, for example, of the lowering of the arm, venous blood shifts into the digital venous pools. As a consequence of volume shifts in the low pressure venous vasculature, the venous pooling in the finger generates signals irrelevant to the actual measurement, masking the desired information.

Therefore, the applied static pressure field is preferably sufficient to prevent pooling of venous blood in the distal end of the digit, but to allow pulsatile blood delivered by the arteries to be returned via the veins. That is, the pressure should be sufficient to prevent free venous flow due to, for example, hydrostatic pressure and shock waves, but to allow the veins to carry blood delivered by the arteries out of the finger. The pressure required to prevent venous pooling may differ from person to person. However, it should preferably not exceed about 10% above such person's diastolic pressure.

In order to obtain a clearer signal, the pressure should also preferably be sufficient to partially unload the wall tension of, but not to occlude, the digit arteries when the digit is near heart level. This allows the arterial wall to move freely to accommodate the pulsatile blood delivery of the heart. Preferably, the applied pressure should be slightly above the maximum pressure in the veins when the hand is fully lowered.

While the appropriate pressure may vary from person to person, a pressure from 30 mmHg to about 10% above diastolic pressure may be used to satisfy both of the above objectives. Clinically, it has been determined that a pressure of approximately 70 mmHg represents the maximal venous pressure level one would expect to find in a tall person's finger when the hand is maximally lowered below the heart level. Such pressure would therefore be sufficient to counterbalance venous pressure in all other circumstances, and effectively keep the veins capacitance in check at a level equaling the arterial throughput, effectively rendering the veins as passive conduits as opposed to volume reservoirs.

Accordingly, the pressure of approximately 70 mmHg is particularly suitable for preventing venous blood pooling and venous shock wave transmission.

As will be described more particularly below, finger probe 2 is used for measuring changes (as a function of time) in volume of the monitored end of the digit accompanying blood pressure waves. This measurement of volume change may then be processed, as to be described below, to detect or monitor a physiological state or medical condition of the subject.

FIGS. 2–4 illustrate further embodiments of the finger probe of the present invention. To simplify the description, those elements in the finger probe illustrated in FIGS. 2–4 which correspond to the above-described elements in the finger probe 2 of FIG. 1 are correspondingly numbered.

Figure 2A:
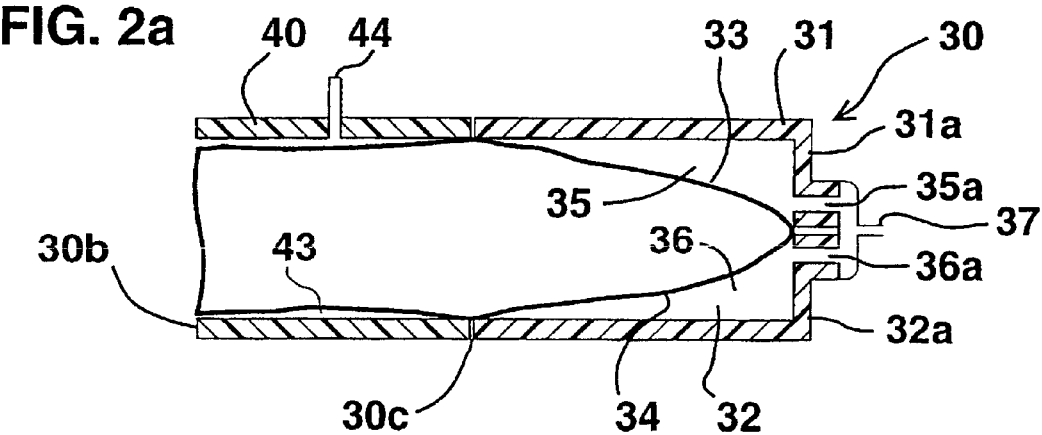
FIGS. 2a and 2b illustrate another embodiment of the probe of FIG. 1.
Figure 2B:
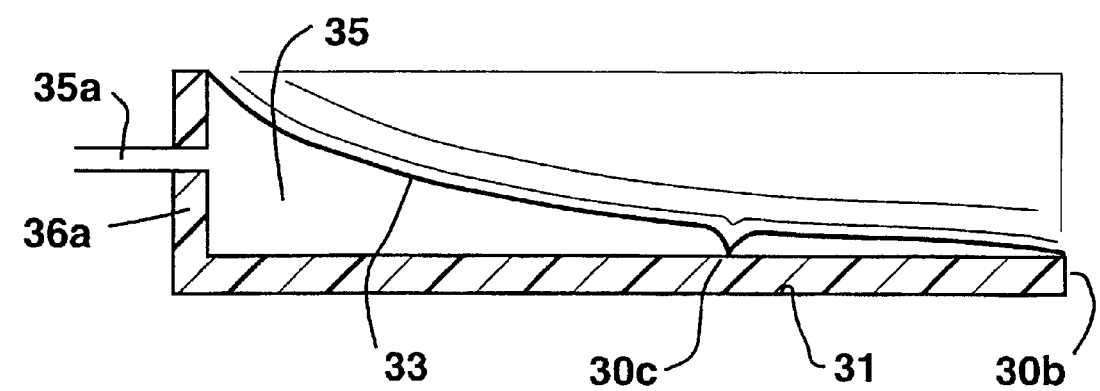

An important feature in the construction of the finger probe 30 illustrated in FIGS. 2–4 is that it includes a thimble-shaped end cap constituted of a plurality of sections. As illustrated in FIGS. 2a and 2b, each of the two semi-cylindrical sections 31, 32, is formed with a cavity, which cavities together define the tubular socket for receiving the subject's finger. Each semi-cylindrical section 31, 32, is formed at one end with a partial end wall 31a, 32a, of partial circular or ellipsoidal configuration, together forming a circular or ellipsoidal end wall. The opposite end of each section is open.

Each casing section 31, 32 includes a planar deformable membrane 33, 34, which membranes together define the equivalent of the deformable tubular membrane for receiving the subject's finger. Each membrane 33, 34, is of a substantially 4-sided configuration and is secured (e.g., by glue or weld) along one transverse edge to the end walls 31a, 32a of the respective casing section, along the opposite transverse edge to the open end 30b of the respective section, and along the two longitudinal edges to the side edges 30c of the respective section. The two casing sections 31, 32 may be secured together by glue or in any other suitable manner (FIG. 2a).

Figure 9:
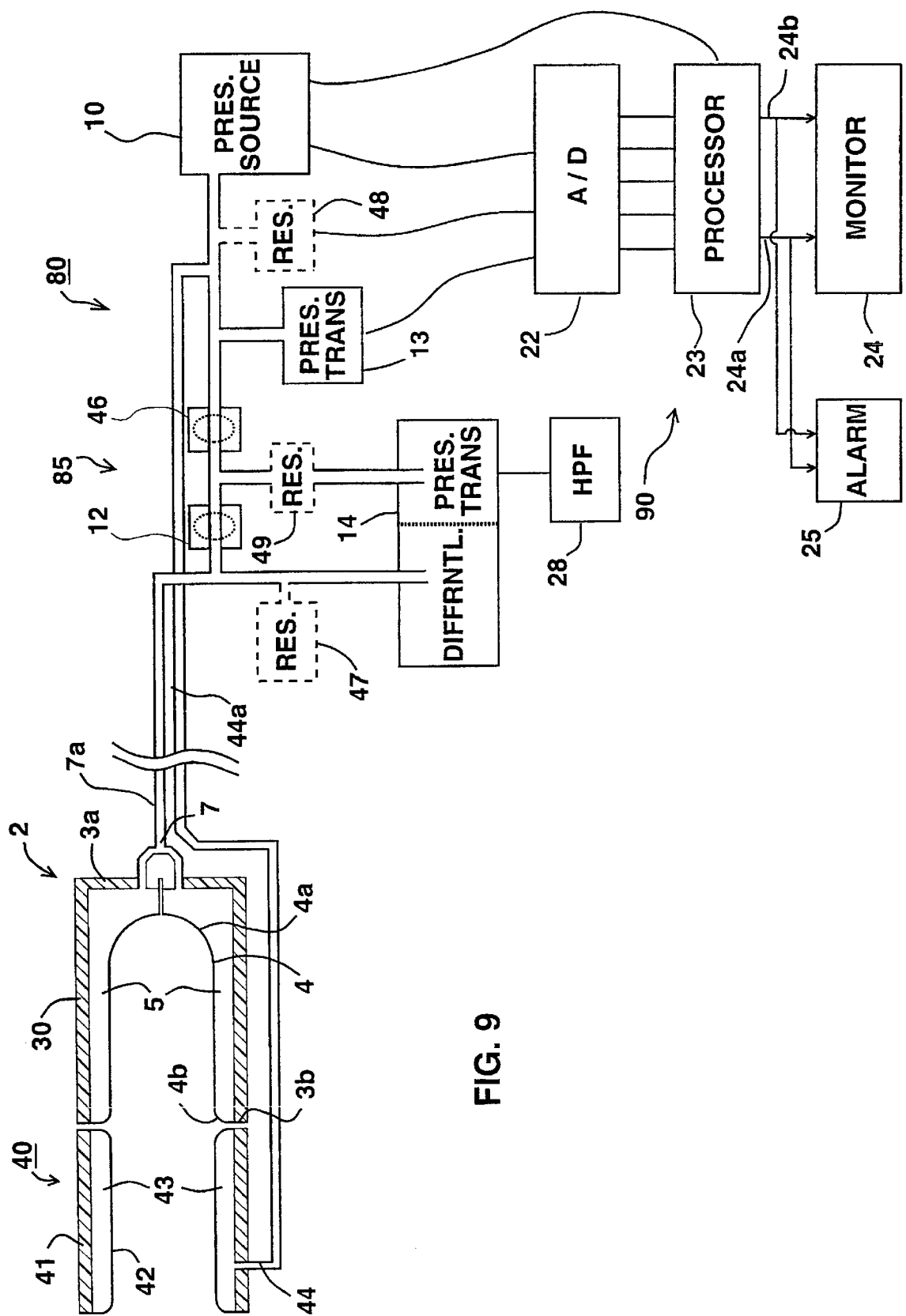
FIG. 9 is a diagram illustrating an embodiment of the entire system including the probe according to the present invention.

Membrane 33 thus defines, with its casing section 31, an expansible chamber 35 having an inlet port 35a (FIG. 2a); and membrane 34 defines, with its casing section 32, an expansible chamber 36 having an inlet port 36a. The two inlet ports 35a, 36a are connected together by conduit 37 to the pressure source 10 (FIG. 9).

Another, substantially annular, chamber 43 is defined by the section of membranes 33 and 34 which extends from side edges 30c to open end 30b. This chamber, 43, can have fluid communication to chambers 35 and 36 and be pressurized via inlets 35a and 36a. Alternatively, chamber 43 may be completely sealed from chambers 35 and 36 and be independently pressurized via inlet 44.

In the single-section construction of the finger probe illustrated in FIG. 1, the axial force caused by the pressure within chamber 5, and which tends to produce an axial movement of the probe with respect to the subject's finger, is countered by the provision of the elastic strings 6. This prevents popping-off of the probe, and minimizes artifacts and erroneous readings caused by axial movement of the probe with respect to the finger, particularly when the subject is in active motion such as during exercise.

On the other hand, according to the embodiment exemplified in FIGS. 2a and 2b, the multi-section construction of the finger probe 30 firmly fixes the probe to the subject's finger against both axial and radial movements. This is because the outer periphery of each of the two membranes 33, 34 is restrained from inward displacement by the casing sections 31, 32 to which the membranes are secured, such that the pressure within the chambers closed by the membranes displaces the central region of each membrane inwardly to a greater degree than their outer peripheries. The inwardly displaced central regions of the two membranes thus produce a two-region clamping action on the opposite sides of the subject's finger, which firmly clamps the probe to the subject's finger. This firm clamping action significantly reduces the danger of pop-off, prevents finger rotation relative to the outer case, prevents the finger from bending, improves the accuracy of the probe in measuring finger volume changes accompanying blood pressure waves, and stabilizes the output signal particularly during exercising.

In the embodiment depicted in FIG. 1, end effects caused by the open end 4b of the membrane 4 can degrade the accuracy of the signal, primarily because the pressure field may taper off towards its open border. Accordingly, it is desirable to isolate the membrane 4 from such end effects. This can be done by adding a pressure cuff to the finger probe 2. The pressure cuff can be made integrally or separately from the casing 3, as demonstrated by the following embodiments. In the embodiment of FIG. 2a, the pressure chamber 43 can be isolated from chambers 35, 36 at periphery 30c. Using such a construction edge effects at the open end 30b will effect the pressure inside chamber 43, but will not reach chambers 35, 36. Therefore, the measurements can be taken only with respect to chambers 35, 36 to avoid edge effects.

As can be understood from the above, the beneficial effects of the pressure applied by chambers 35 and 36 decrease towards the open end 30b of the finger probe. Therefore, the pressure field is effectively extended beyond the measurement site by including the pressure cuff.

Figure 3A:
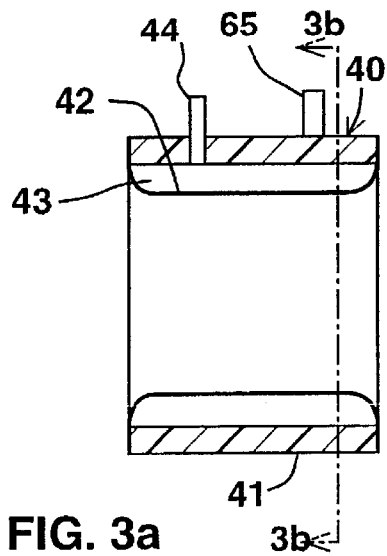
FIG. 3a is a length-wise cross-sectional view illustrating a pressure cuff constructed in accordance with an embodiment of the present invention.
Figure 3B:
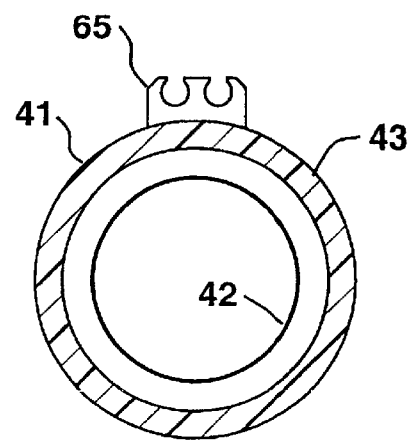
Figure 4A:
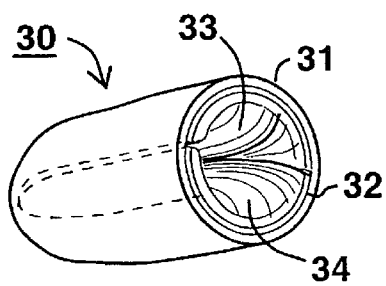

According to a further embodiment of the present invention, the chamber 43 depicted in FIG. 2a is constructed independently of the casing sections 31 and 32. Such an embodiment is exemplified in FIGS. 3a and 3b, FIG. 3b being a cross-section at line A'—A' of FIG. 3a. As shown in FIGS. 3a and 3b, a substantially cylindrical pressure cuff 40 is constructed of rigid cylinder 41, and membrane 42 attached thereto. The space between the membrane 42 and the cylinder 41 defines a chamber 43, which can be pressurized via inlet 44. The pressure cuff 40 can be secured to the open end of the end cup shown in FIG. 4a, formed by casing sections 31 and 32. This is demonstrated in FIG. 4b.

Figure 4B:
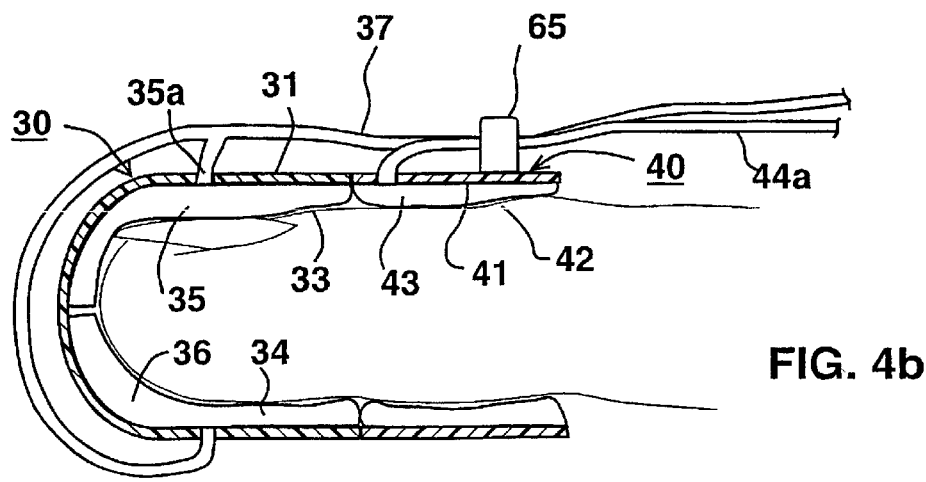
FIG. 4b illustrates the pressure cuff of FIG. 3 as it is used in conjunction with the end-cup of FIGS. 2a and 2b.

Also shown in FIGS. 3a, 3b, and 4b is a tubing retainer 65. The tubing retainer is advantageously provided to prevent noise which may be caused by tugging on the tubing. Preferably, the tubing retainer should be utilized in all of the embodiments of the inventive finger probe.

Figure 5A:
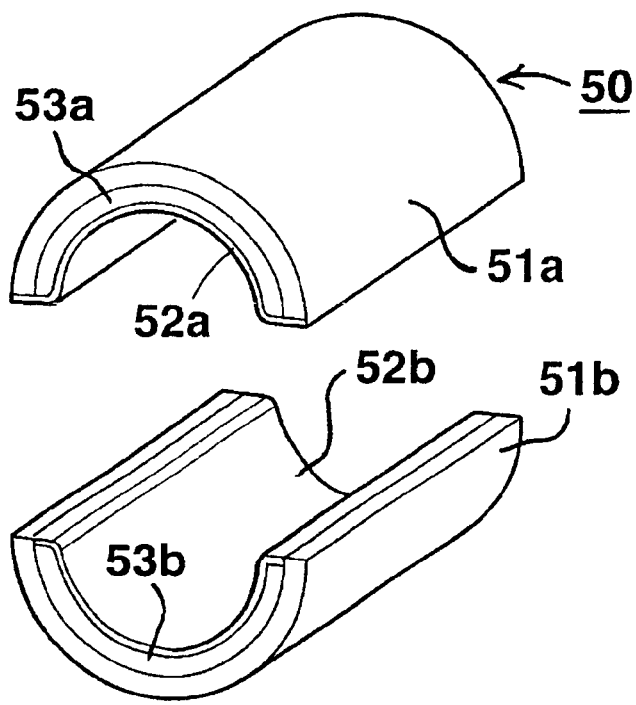
FIG. 5 illustrates another embodiment of the pressure cuff according to the present invention.
Figure 5B:
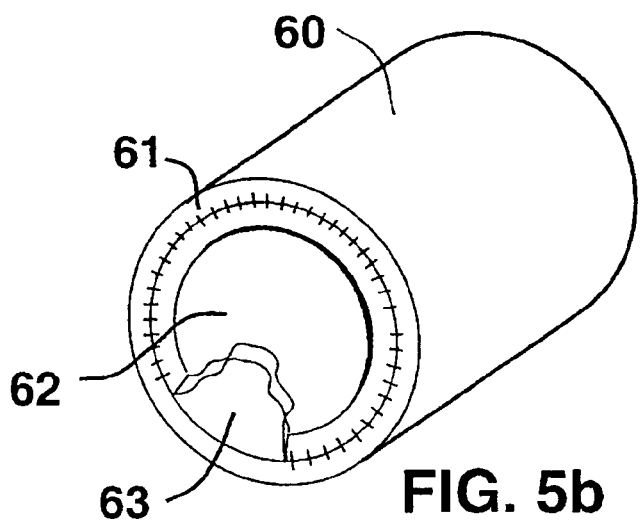

FIG. 5 illustrates another embodiment of the annular pressure cuff 40. According to this embodiment, the pressure cuff is of a multi-section construction similar to the multi-section construction of the pressure cap 30 in FIGS. 2a and 2b. That is, the construction of FIG. 2a will effectively result in a similar pressure cuff if isolation is provided at periphery 30c. Thus, the annular pressure cuff 50 illustrated in FIG. 5 is constituted of two outer, rigid, semi-cylindrical sections 51a, 51b, with each section including an inner deformable membrane 52a, 52b secured to the respective section so as to define therewith two semi-annular expansible chambers 53a, 53b.

FIG. 6 illustrates yet another embodiment of the annular pressure cuff. According to this embodiment, the annular cuff 60 includes an outer ring 61 which is of flexible, non-stretchable material such as non-stretchable plastic, and a cylindrical membrane 62 secured thereto to define the annular chamber 63 for applying the pressure to the subject's finger.

FIGS. 6a–6e illustrate embodiments wherein the pressure cuff is used to allow measurements without the need for the bladder. As shown in FIG. 6a, the finger probe 2 basically includes the end cap 30, having situated therein the pressure cuff 40. As depicted in FIG. 6c, when a finger is inserted into the finger probe 2, a chamber $C_0$ is defined by the casing and the finger. The conduit 44a is used to pressurize the chamber 43 defined by the pressure cuff 40, so as to provide a tight seal. This allows application of pressure by conduit 37 into chamber $C_0$.

As shown in FIG. 6b, one may also use the two-halves construction detailed above. Additionally, it is preferable to provide adhesive layer or ring 90 to suppress movement of the probe and increase air-tightness. Another layer of adhesive material 91 is provided on the inner surface of the tip of the end cap 30, to further assist in preventive movement of the finger probe with respect to the finger.

Optionally, air-tightness may be ensured by providing a circumferential open flange of compliant membranous material 95. The opening in the membrane should be smaller than the smallest diameter of a finger to be inserted, so that the membrane would provide a seal when the finger is inserted. A similar flange, 96, can be provided on the other side of the pressure cuff.

Figure 7:
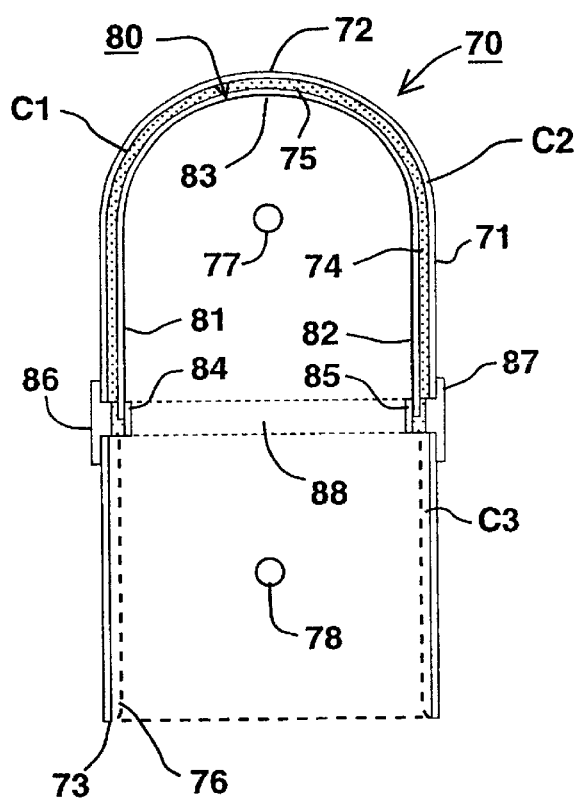
FIGS. 7, 7a and 7b illustrate the preferred embodiment of the finger probe of the present invention, wherein the end-cup and the pressure cuff are integrated into a single finger probe.
Figure 7A:
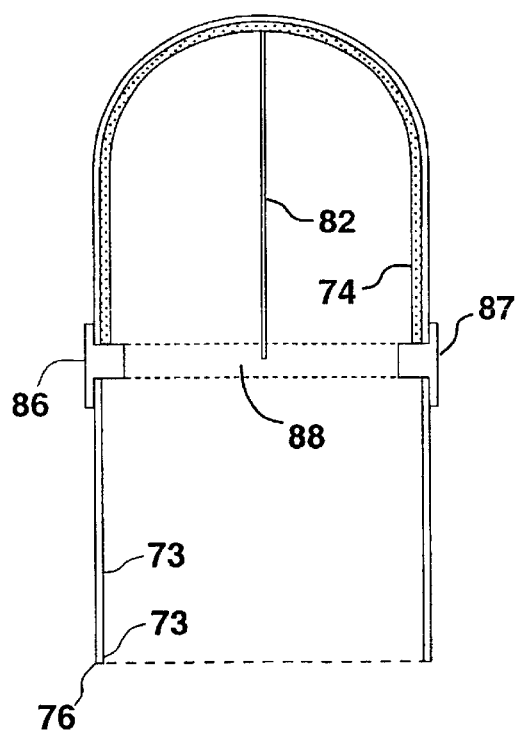
Figure 7B:
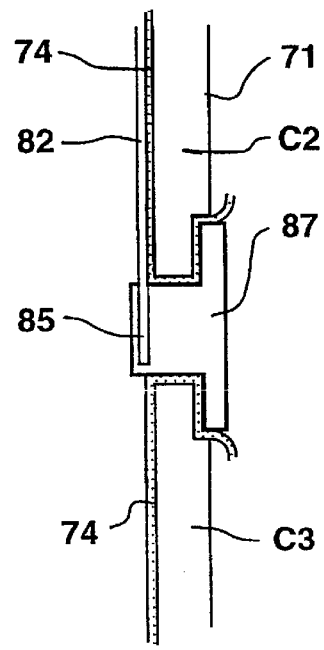

FIGS. 7, 7a and 7b illustrate in detail the construction of the probe according to the preferred embodiment of the invention, wherein the pressure cap and the annular pressure cuff are integrated into a single unit, generally designated 70. Unit 70 includes a single rigid tube 71 closed at one end by a semi-spherical or semi-ellipsoidal end wall 72, and open at the opposite end 73 for receiving the finger of the subject. A deformable tubular membrane 74 is received within tubular casing 71. Membrane 74 is similarly closed at one end 75 and open at the opposite end 76 for receiving the subject's finger.

Tubular casing 71 further receives a U-shaped rigid restraining bar, generally designated 80, having a pair of parallel legs 81, 82 joined by a semi-circular midsection 83. The outer ends 84, 85 of the two parallel legs 81, 82 are secured to inserts 86, 87 fastened within the wall of the rigid tube 71. The two inserts 86, 87 are carried by a circular pressure band 88 secured within the device and pressing the respective midportion of the tubular membrane 74 firmly against the inner surface of the tubular casing 71. The open end 76 of the tubular membrane 74 is secured to the open end 73 of the tubular casing 71, for example, by gluing or by another pressure bond.

It will be seen that such a construction defines three chambers, namely: two chambers, $C_1$, $C_2$, between the tubular membrane 74 and the tubular casing 71 on the opposite sides of the U-shaped restrainer bar 80; and a third chamber $C_3$ of annular configuration between pressure band 88 and the open ends of the tubular membrane 74 and the rigid casing 71. By applying pressure against the walls of the casing 71, the circumferential band 88 prevents fluid communication between the third chamber $C_3$ to the two chambers $C_1$ and $C_2$. On the other hand, the semi-circular midportion 83 of the restrainer bar 80 is preferably spaced somewhat inwardly of the inner surface of casing end wall 72 so as to provide direct fluid communication between the two chambers $C_1$, $C_2$. Casing 71 may be formed with one or two holes 77 serving as fluid ports for chambers $C_1$, $C_2$, and a further hole 78 serving as a fluid port for chamber $C_3$. However, it should be noted that if no isolation is provided between chamber $C_3$ and chambers $C_1$ and $C_2$, then solenoid valve 46 (to be described later) may be eliminated.

It will thus be seen that when fluid pressure is applied to chambers $C_1$, $C_2$, the outer periphery of each of the two sections of the tubular membrane 74 engaged by restrainer bar 80 will be restrained from inward displacement. Thus, the pressurized fluid within chambers $C_1$, $C_2$ will displace the central region of each of the membrane sections inwardly to a greater degree than the outer periphery of the respective membrane section, producing a two-point clamping action and preventing pop-off and axial and rotational movement of the finger relative to the device. -The portion of tubular membrane 74 not covered by restrainer bar 80 defines annular chamber $C_3$ which will produce the same type of annular pressure cuff as described above with respect to annular pressure cuff 40.

The device illustrated in FIGS. 7, 7a and 7b is advantageous in that the restrainer bar 80 reduces movement artifacts because the membrane walls of the sections of the membranes in the two chambers $C_1$, $C_2$ move in unison if the finger moves relative to the device. That is, when the membrane sections are individually glued to their respective casing sections as described above with respect to FIGS. 2a and 2b, the movement of one diaphragm section is not transferred to the other, thereby producing movement artifacts. On the other hand, when the two membrane sections are parts of the same membrane as in FIG. 7, they tend to move together, thereby reducing such movement artifacts.

Another advantage of the FIG. 7 construction is that a single fluid port is sufficient for supplying the fluid pressure to both chambers $C_1$, $C_2$, since they are interconnected by the space provided by the restrainer bar. In addition, the construction illustrated in FIG. 7 is easier to produce in volume and at a lower cost.

While not depicted, it should be appreciated that the tube retainer 65 can be used in the embodiment of FIG. 7 as well. The tube retainer can be affixed to the outer shell of the probe, or may be a part of one of the inserts 86, 87.

Glove Probe Construction

Figures 8, 8A:
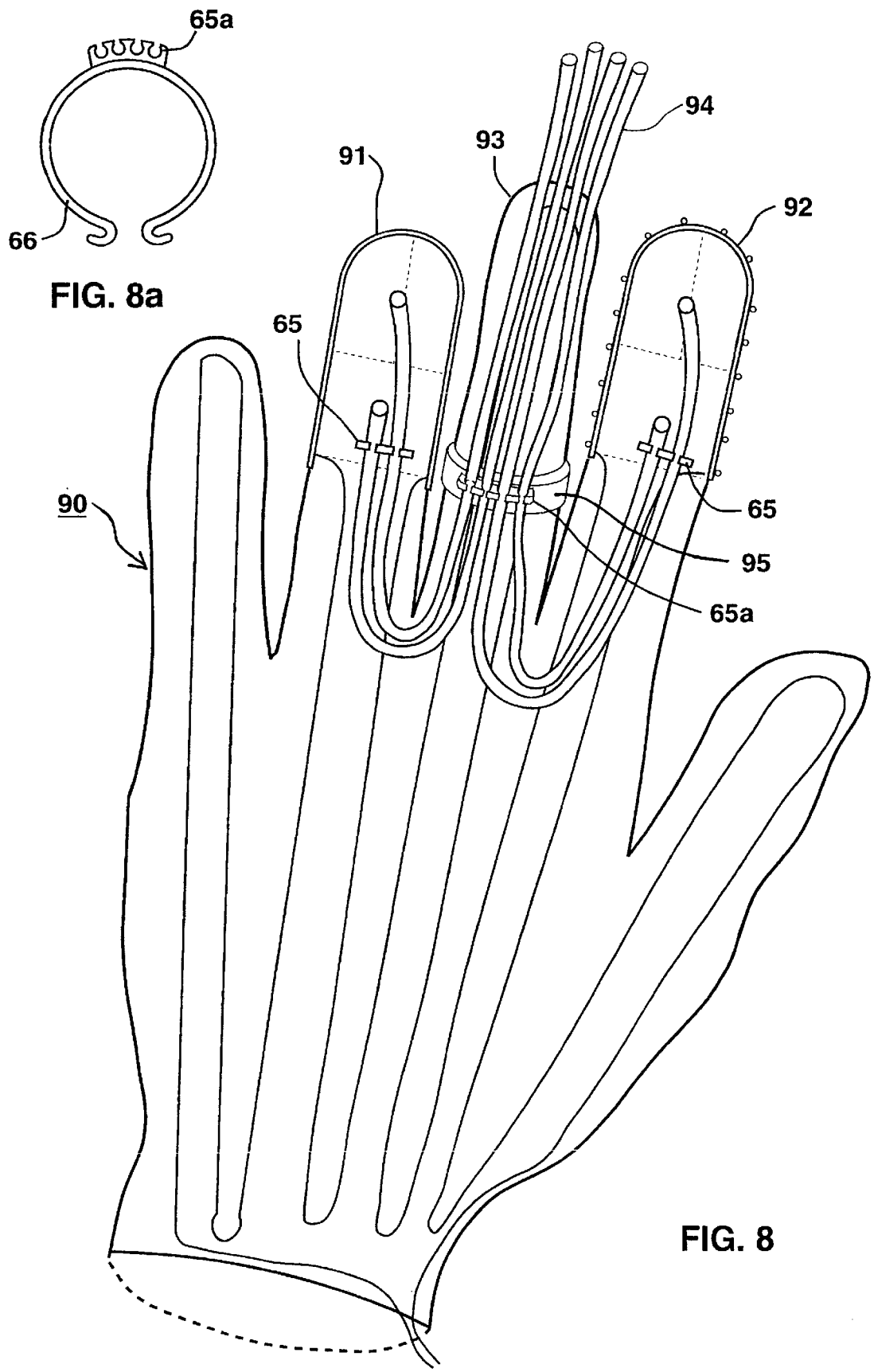
FIG. 8 illustrates an embodiment of the present invention wherein a plurality of finger probes are incorporated into a glove.
FIG. 8a depicts a tube retainer for a finger not having a probe thereon.

FIG. 8 illustrates the finger probe incorporated into a glove, generally designated 90, to be worn by the subject. In the illustrated construction, two of the fingers of the glove incorporate the probe, shown at 91 and 92, respectively. A third glove finger 93 may be used for supporting the fluid tubes, e.g., air tubes, for pressurizing the various chambers in each of the volume-measuring devices. Also, the glove may include only the one or two fingers incorporating the probe, together with a band for attachment to the subject's hand or wrist.

An advantage of the glove construction illustrated in FIG. 8 is that it conveniently permits the probe to be applied to two (or more) fingers at one time so that two (or more) outputs can be processed to obtain more reliable results, e.g., as a consistency check, by selecting the higher output, or by averaging the outputs. On the other hand, each of the probes can be used for different measurement. For example, one probe can be used to monitor peripheral vasoconstriction, while the other one to monitor the blood pressure of the patient. By measuring peripheral resistance and blood pressure at the same time one can understand significantly more about the overall hemodynamic state and the hemodynamic changes of the patient, than by measuring either one of these parameters alone.

In addition, the glove construction helps to stabilize the tubing, and prevents the transmission of forces to the volume measuring device as a result of tugging on the tubes. Particularly, in addition to the tube retainers 65 provided on the probes themselves, an additional tube retainer 65a (FIG. 8a) can be provided on an open ring 66 to be placed on a finger not having a probe thereon. It should be appreciated that tube retainer 65a and open ring 66 can be used independently of the glove embodiment.

Also, the glove (or any of the finger probes) can optionally be fitted with heating elements should one wish to heat the entire hand. Heating the measurement site may be used to modify the underlying degree of vascular tone. This could allow setting of the vascular tone to a point at which modulations by the body's control could be better measured, since a preexisting high level of vasoconstriction may prevent further measurable increase in vasoconstriction.

The Overall Apparatus

FIG. 9 illustrates the preferred embodiment of the apparatus for detecting myocardial ischemia according to the present invention. In this form, the present inventors refer to the device as the IschemoGraph and to the inventive process as IschemoGraphy.

As illustrated in FIG. 9, the finger probe 2 comprising the thimble-shaped end cap 30 and the pressure cuff 40 is connected to a pneumatic system, generally designated 80, which is in turn connected to a processing system, generally designated 90. The pneumatic system 80 generally comprises a pressure source 10 connected to a pneumatic tubing system, generally designated 85. The tubing system includes tubes 7a and 44a, which deliver the pressure from the pressure source to the finger probe 2, and electronic solenoid valves 12 and 46, which can be controlled by the processor 23 to be described later. Of course, solenoid valves 12 and 46 can be replaced by mechanical valves which can be controlled manually.

The pneumatic system 80 further includes a pressure transducer 13 for monitoring the pressure applied by source 10, and a differential pressure transducer 14 measuring the difference between the variable pressure in the finger probe chambers and the constant pressure existing between valves 12 and 46. Optionally, the pneumatic tubing 85 is further provided with reservoirs 47, 48 and 49, shown in FIG. 9 in broken line to signify that it is optional equipment. One or any number of such additional reservoirs may be provided to decrease the sensitivity of volume changes in the respective chambers to small volume losses of gas due to leaks or elasticity of the respective conduit system, and also to reduce the size of the back pressure changes due to the pulse waves.

In FIG. 9, no valve is depicted on the line connecting the pressure source to the tubing of the pneumatic system 80. This is because in the preferred embodiment the pressure source includes internal valve. However, if no such valve is available, it is preferable to add a valve on the outlet of the pressure source 10.

The processing system 90 includes an A/D converter 22, a processor 23, and a monitoring device, generally indicated as monitor 24 and alarm 25. The processing system is responsible for controlling the operation of the overall system, such as controlling pressure source 10 and solenoids 12 and 46, and also processes the detected signals to provide a decipherable output.

Monitoring Procedure

As can be understood from this specification, the inventive apparatus can be used to detect cardiopulmonary distress, particularly myocardial ischemia, in various environments. That is, the apparatus can be used for monitoring during an exercise test, it can be used for monitoring during balloon angioplasty, and it can be used for monitoring during sleep. However, in all cases the basic operation of the system remains the same.

The operation of the system will now be described with reference to FIG. 9. In order to perform a diagnostic procedure, the valves 12 and 46 are first open and the chambers 5 and 43 of the finger probe are evacuated to allow the patient to insert his finger into the probe. Then, the pressure is raised to a pressure which is sufficient to unload the arterial walls and to prevent venous pooling. The pressure applied by source 10 is measured by a pressure transducer 13 upstream of valves 12 and 46. In the preferred embodiment, the pressure in the pneumatic compartments is automatically raised to 70 mm Hg.

At this point, valves 12 and 46 are closed, so that the pressure in the right chamber of pressure differential transducer 14 is kept constant. On the other hand, the pressure on the left chamber of transducer 14 varies depending on the pressure inside chamber 5 of the finger probe 2. Notably, for detection of peripheral vasoconstriction, no calibration of the inventive device is necessary, since the measurement is comparative with the patient's own baseline results observed during the test.

In order to obtain good results, relative immobilization of the hand being tested is desirable. During the various exercise stress tests this is usually achieved by holding the hand in a stable position and avoiding excess movement of the hand. Immobilization is generally not a problem during PCTA, where the apparatus is valuable for both monitoring ischemia during occlusion and monitoring post-dilatation patency of the artery, nor during sleep monitoring.

As can be understood from the description so far, changes in the volume of the subject's finger due to arterial blood pressure pulse waves produce an expansion or contraction of chamber 5, and a corresponding decrease or increase in the gas pressure within chamber 5. As noted above, chamber 5 is connected via its port 7 and tube 7a to the pneumatic tubing 85. However, since valve 12 is closed, the pressure changes affect only the pressure within the left chamber of differential-pressure sensor 14. The differential pressure sensor 14 detects these pressure changes and provides an output corresponding to the pressure changes.

The A/D converter 22 shown in FIG. 9 receives the analog outputs of pressure transducers 13 and 14, and converts them into digital form before introducing them into a CPU processor 23. The processor 23 processes the measured finger volume (or optical density) changes to produce output 24a of the volume measurements, and/or an output 24b of the changes in the volume measurements with respect to time. Either one or both measurements can be displayed on the monitor 24 (such as a CRT or an LCD). Alternatively, these outputs can be displayed on separate monitors. Further, these measurements can be transmitted for display at a remote location, such as a nursing monitoring station.

If the displayed output 24b shows a change in the measured volume exceeding a predefined cut-off point, indicating peripheral vasoconstriction, this will be immediately seen by the observer viewing monitor 24. Optionally, an alarm 25 (e.g. audio or visual) may be actuated if this predetermined drop in measured volume occurs, to immediately alert the attendants.

The peak to trough amplitude of the signal is generally proportional to the arterial pulsatile volume changes, and will decrease upon peripheral vasoconstriction. Therefore, when the system of FIG. 9 is used for detecting peripheral vasoconstriction, the observer would be interested in relative changes of the amplitude of the trough to peak values, as opposed to the absolute values of the pressure. Accordingly, in the preferred embodiment, a high pass filter 28 is provided to filter the output of the transducer 14 and improve the signal to noise ratio.

As explained above regarding the finger probe, it is preferable that the finger probe include an annular pressure cuff 40 coaxial with and contiguous to the end cap 30, on the proximal (heart) side of the device. The main purpose of the pressure cuff is to extend the boundary of the constant pressure field beyond the borders of the sensing probe, so as to avoid edge effects. Chamber 43 of the pressure cuff is also filled with a pressurized gas via a port 44; however, solenoid valve 46 isolates conduit 44 from transducer 14. Cuff 40 thus extends the static pressure field for a distance in the proximal (heart) direction from the site of measurement of the finger volume changes accompanying blood pressure waves. The annular pressure cuff 40 acts as a tourniquet which, together with the pressure field produced in the thimble-shaped end cap 30, prevents venous pooling in the distal end (particularly the most distal phalange) of the finger. It also substantially prevents uncontrolled venous backflow; and further, it partially unloads the wall tension of, but does not occlude, the arteries in the distal end of the finger when the finger is at heart level. While the pressure in the pressure cuff may differ from that in the sensing chambers 35, 36, it should not exceed it.

Manual Pneumatic Control System

Figure 10:
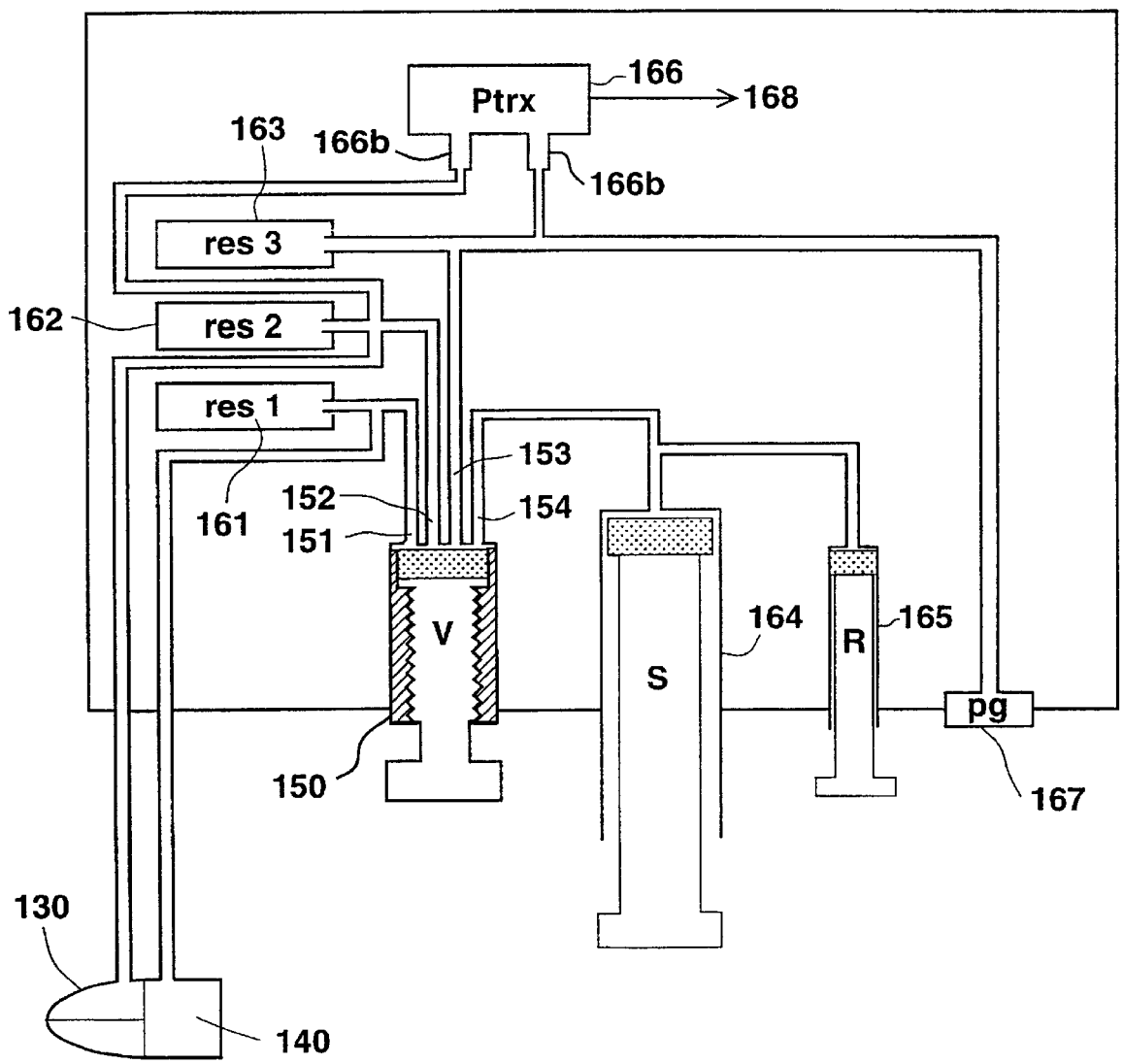
FIGS. 10 depicts a manual pneumatic system replacing the automatic pneumatic system depicted in FIG. 9.

FIG. 10 illustrates a manual pneumatic control system, which may be used instead of the automatic pressure source 10, for presetting and applying the static pressure field to the end cap 30 and annular cuff 40 of the finger probe. The system illustrated in FIG. 10 includes a four-way, screw-mounted presetting valve assembly 150 having four ports 151–154 leading from a common chamber in the valve assembly. Port 151 communicates with a reservoir 161 which in turn communicates with the annular cuff 140; port 152 communicates with a second reservoir 162 which in turn communicates with the pressure cap 130; port 153 communicates with a third reservoir 163; and port 154 communicates with a syringe 164 and with a release valve 165 leading to the atmosphere. A differential pressure transducer 166 corresponds to transducer 14 of FIG. 9, and it communicates with reservoirs 162 and 163 to compare the pressure therebetween. Transducer 166 also communicates with a pressure gauge 167, which replaces the transducer 13 of FIG. 9. The output of the transducer 166 is provided to the processing system in a similar manner to that described with respect to FIG. 9.

The system illustrated in FIG. 10 is operated as follows:

First, the presetting valve assembly 150 is opened to establish communication between all the ports 151–154. Release valve 165 is then opened to connect the system to the atmosphere. Syringe 164 is drawn to the middle of its range; release valve 165 is closed; and syringe 164 is then withdrawn to the maximum extent to create a vacuum within the common chamber of presetting valve assembly 150.

The finger probe is then applied to the subject's finger. Syringe 164 is pressed inwardly until the target pressure is achieved; and presetting valve assembly 150 is then closed, so that inlet 166a is held at a constant pressure, while the pressure at inlet 166b would vary depending on the pressure inside chamber 130 of the finger probe. Therefore, any changes in pressure sensed by the transducer 166 would correspond the arterial blood volume, and a corresponding signal is output 168 by the transducer 166, for processing by the processor 23.

Arterial Tone Sensor

In the above detailed examples of the finger probe according to the present invention, the peripheral arterial vasoconstriction was sensed pneumatically, i.e., by sensing changes in pressure caused by the change in volume of the blood in the peripheral arteries. However, it should be appreciated that other changes in the skin or other extremity of the patient accompanying changes in the peripheral arterial tone in response to cardiopulmonary distress may also be measured. As examples: optical density or surface-reflectivity of the outer end of the finger (or toe) or the skin in other areas of the body may be measured using a light source and light collector; electrical resistivity may be measured to determine the galvanic skin response; and blood velocity flow may be measured by a Doppler ultrasound device, laser Doppler device, or other flow meter devices.

Figure 11:
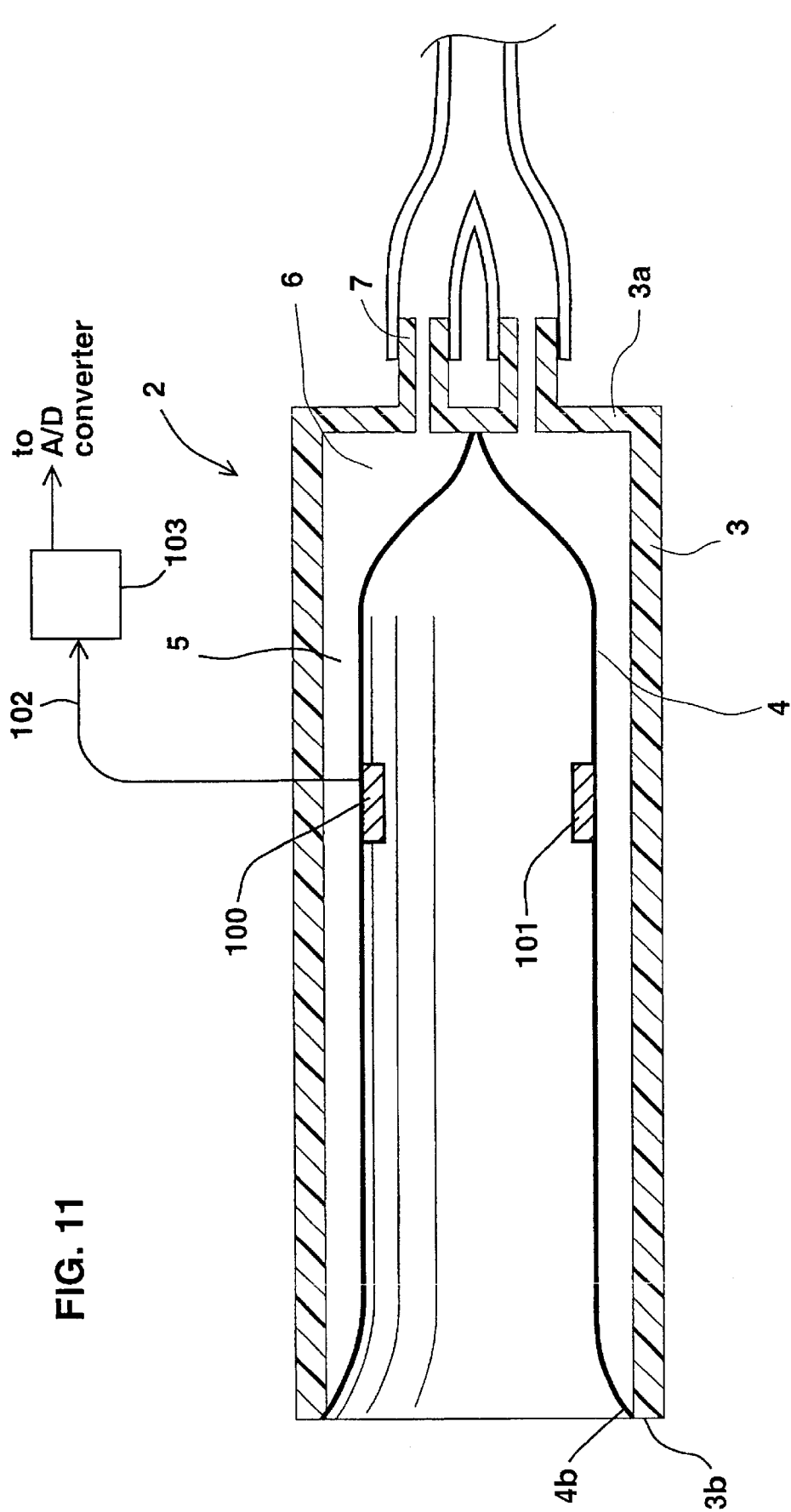
FIG. 11 depicts another embodiment of the finger probe of the present invention, wherein the probe includes an optical sensor.

FIG. 11 illustrates an apparatus similar to that of FIGS. 1–7 except that changes in the optical density are directly measured to provide a measurement of the changes in the finger accompanying the blood pressure waves. To facilitate understanding, the same reference numerals are used for corresponding parts as in FIGS. 1–7.

Thus, in the apparatus illustrated in FIG. 11, chamber 5 is pressurized to a fixed predetermined value, as described above with respect to FIG. 9. In this case, however, the tubular diaphragm 4 defining chamber 5 is provided on one side with a light source 100, and on the opposite side with a light receiver 101, such that pulsatile blood volume changes in the finger received within the tubular diaphragm 4 will be detected as changes in optical density by the light receiver 101. This information is fed via conductors 102 to an amplifier circuit 103 where it is amplified and filtered, and then fed to the A/D converter 22 for processing by the processor 23 as described above.

In the arrangement illustrated in FIG. 11, the measurement site, namely the location of the light source 100 and light receiver 101, is considerably inward of the open end of the rigid casing 3 of the probe 2 which applies the static pressure field uniformly around the outer end of the finger, and therefore the annular pressure cuff (40, FIG. 9) need not be included for this purpose. However, if it is desired to locate the light source and light collector closer to the open end of the rigid casing of the probe 2, the annular pressure cuff (corresponding to pressure cuff 40 in FIG. 9), may also be used in the system illustrated in FIG. 11.

Clinical Data

During PTCA (balloon angioplasty) a part of the blood supply to the myocardium is knowingly shut down for a known period of time. Under no other circumstances can one be as clearly aware of the timing, location and extent of the interference of the coronary blood flow. Therefore the inventive IschemoGraph was evaluated in a number of patients during such procedures.

There are theoretical limitations to the ability to define the effects of balloon inflation related interruption of coronary blood flow. For example, if a segment of a coronary artery is substantially occluded, the act of inserting the catheter carrying the balloon may of itself greatly reduce the remaining orifice, such that further encroachment of the orifice by inflating the balloon may not alter blood flow as greatly as might be expected. Furthermore, balloon expansion by compressing surrounding myocardium may elicit reflex responses unrelated to the interruption of the coronary blood flow per se.

While such factors could modify the blood flow related effects of coronary PTCA, the findings discussed below clearly support the link between peripheral resistance changes and myocardial ischemia.

Figure 12:
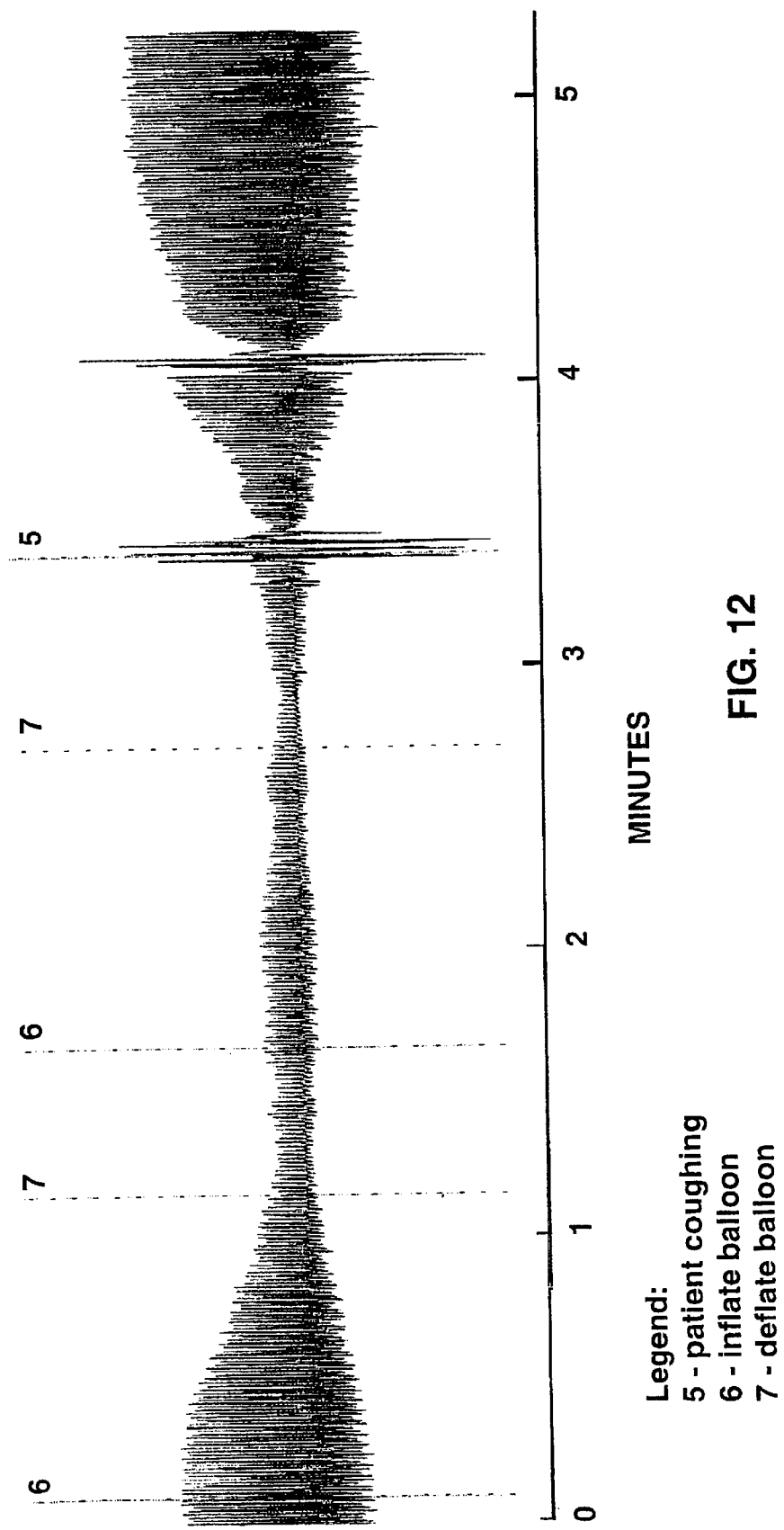

FIG. 12 illustrates the time course of the output signal of the inventive IschemoGraph before, during, and after inflation of a balloon within a coronary artery of a patient free of vaso-active medications. The output corresponds to pulsatile arterial volume changes, i.e., changes in the trough to peak amplitude of the signal correspond to changes in the arterial volume. Thus, a reduction of the peak to trough amplitude would signify vasoconstriction, while an increase in the amplitude would signify vasodilation. The base line for comparison is set as the trough to peak amplitude before provoking the heart to increase its demand for oxygen.

As shown in FIG. 12, approximately at time zero the balloon was inflated. Then, from time zero to just over one minute, a continuous reduction in the peak to trough amplitude of the signal followed, which signifies that inflating the balloon caused peripheral vasoconstriction reaction to the induced temporary ischemia.

At about 70 seconds the balloon was deflated, but was re-inflated again about half a minute later. No significant changes are observed in relation to relatively short period of deflation. That is, upon studying the signal's amplitude from time zero to one minute and that of the signal's amplitude from minute one to minute three, one can deduce that the arterial peripheral tone fell gradually over 30 seconds and then remained relatively stable during the procedure for about one minute. It should be understood, however, that the reference herein to reaction time includes the time it takes to inflate or deflate the balloon.

At time referenced 5 in FIG. 12, the patient coughed, and a rapid and drastic increase in the signal's amplitude is observed. During certain conditions, such as coughing or yawning, a pressure wave propagates through the arteries. Such a pressure wave can be detected by the inventive IschemoGraph and is distinguishable by its relative sharp rise and fall curves, and its short duration.

Figure 13:
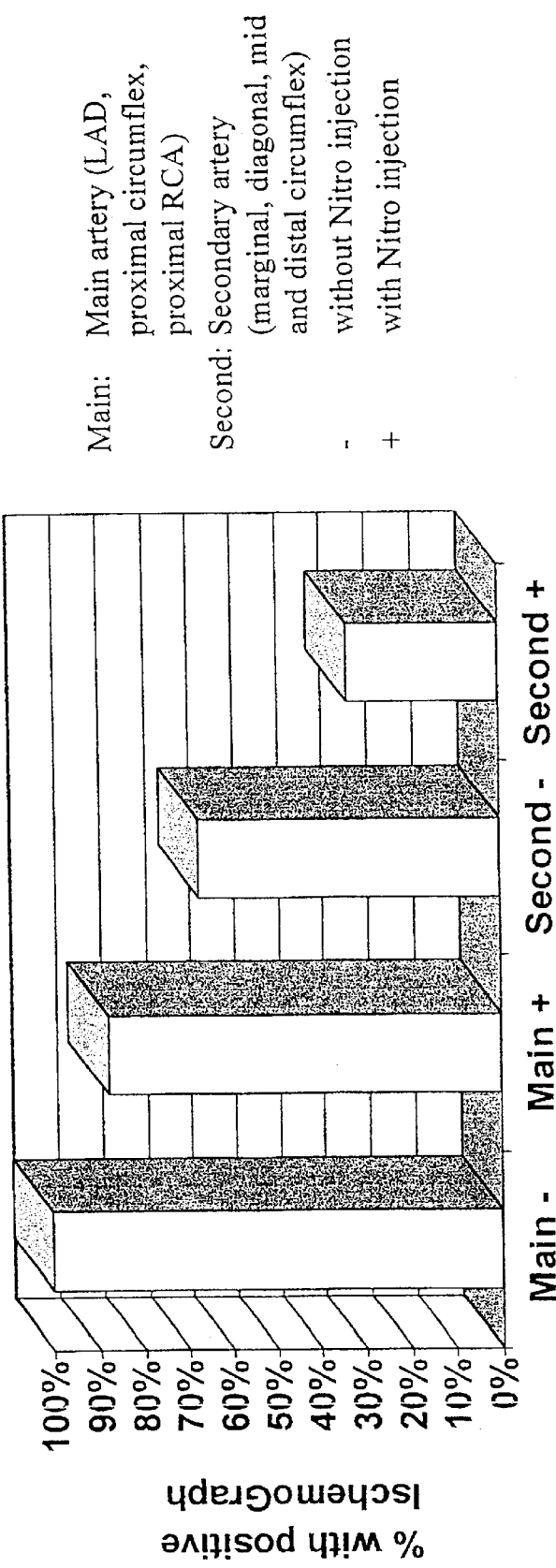

FIG. 13 is a bar graph summarizing the changes in the output signal associated with balloon inflation during 67 PTCA procedures in 29 subjects. In each instance, the change in the value of the signal during inflation was used as a reference value indicating induced ischemia. The signal outputted by the apparatus was indicative of myocardial ischemia in 23 out of 23 cases in which PTCA of a main artery was performed without the administration of nitroglycerine (referenced by a negative (−) sign). When nitroglycerine was administered (referenced by a positive (+) sign), 7 out of 8 patients showed positive responses. The results of PTCA to secondary coronary arteries without and with nitroglycerine are also shown. As could be reasonably anticipated, in these cases, recognition of ischemia was lower.

The apparatus illustrated in FIG. 9 has been used in a clinical studies for detecting myocardial ischemia in patients while undergoing standardized exercise tests, and the results were compared with the results produced when utilizing the Thallium SPECT and ECG techniques of the prior art.

Figure 15B:
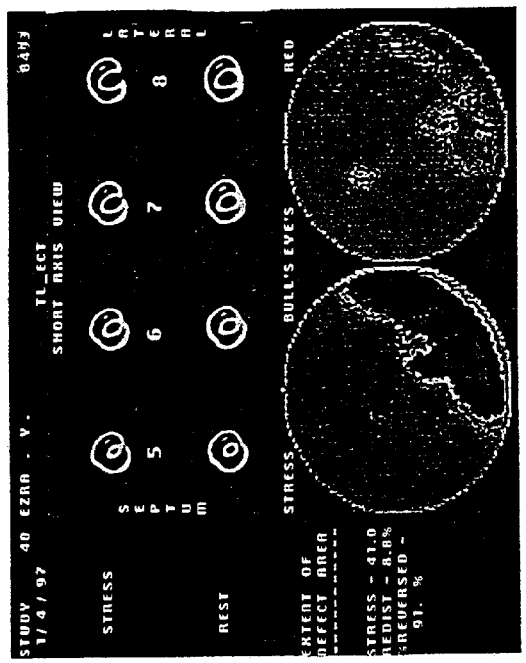
Figure 15A:
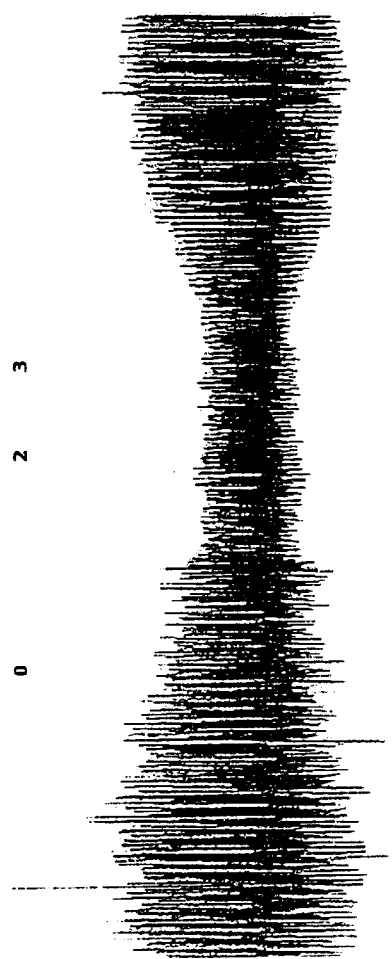

FIG. 14 illustrates the relationship between the results of the inventive IschemoGraph when compared to Thallium SPECT results in 93 patients who underwent standardized exercise stress tests at the Sheba Medical Center and the Kaplan Hospital in Israel. The upper left-hand block indicates that the IschemoGraph identified as positive all the patients (53) identified as positive by the Thallium SPECT. (FIG. 15 depicts exemplary data for one patient for whom both the Thallium SPECT and the IschemoGraph readings provided positive readings.) Thus, the only disagreement between the two methods relates to negative identifications.

Figure 16B:
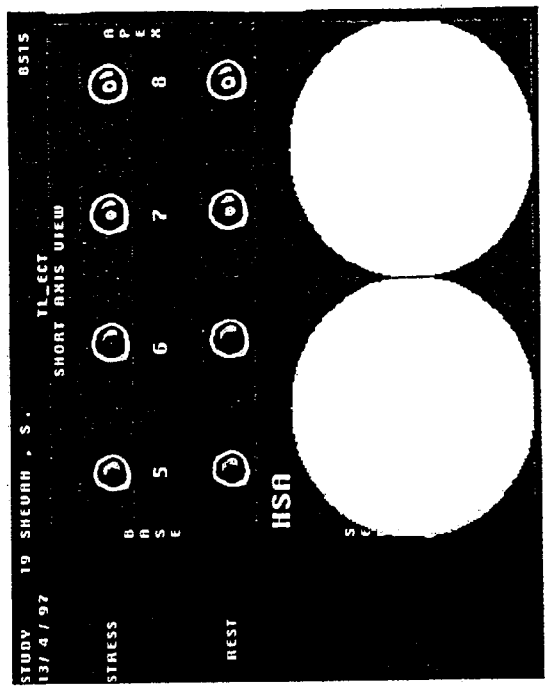
Figure 16A:
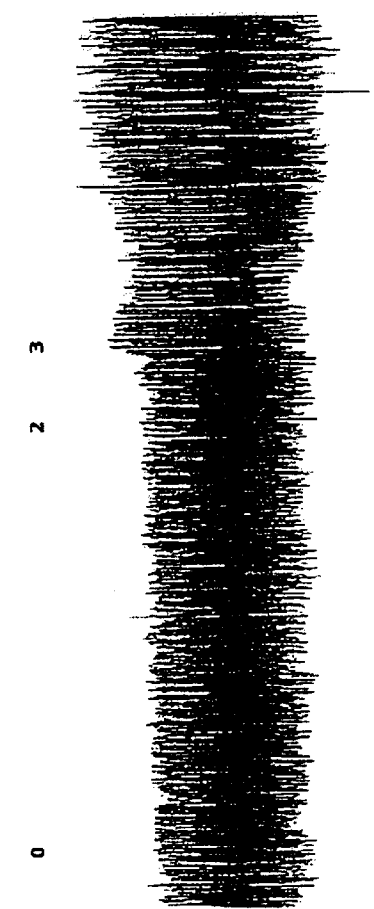

More specifically, as shown on the bottom right-hand block of FIG. 14, of the 40 patients identified by Thallium SPECT as negative, the IschemoGraph also identified 28 as negative. (FIG. 16 depicts exemplary data for one patient for whom both the Thallium SPECT and the IschemoGraph provided negative readings.) As shown in the top right hand corner of FIG. 14, the remaining 12 patients which were identified as negative by the Thallium SPECT were identified as positive by the IschemoGraph. Of these 12 patients, three were referred by their physicians for coronary angiography. In all three of these cases, coronary artery disease requiring medical management was found, confirming the positive finding of the IschemoGraph.

In summary, according to the data provided in FIG. 14, the overall agreement in using the IschemoGraph as compared to the Thallium SPECT technique was 87%, and with regard to the remaining 13% (12 patients), further analysis in the form of coronary angiography was performed on three patients, each of which confirmed the positive Ischemo-Graph findings.

In contrast, FIG. 17 illustrates the results produced by the use of the known ECG technique versus the Thallium SPECT technique, with respect to the previously mentioned exercise stress tests performed on the 93 patients. This comparison is relevant since the ECG technique is the only conventional tool which may be considered for mass screening for myocardial ischemia, and is much less expensive and complicated than the Thallium SPECT. FIG. 17 includes three rows, since the ECG provided certain readings which were ambiguous and inconclusive. As shown, the ECG results were consistent with the Thallium SPECT results in only 50% of the cases.

As shown in the top left-hand block of FIG. 17, the ECG identified only 20 out of the 53 patients identified as positive by the Thallium SPECT, which amounts to only 38% agreement. Moreover, even if all the ambiguous readings of the ECG reported in the second row of the left-hand column were interpreted to be positive, the ECG would still identify only 59% of those identified as positive by the Thallium SPECT.

As shown in the bottom left-hand block, the ECG data identified 22 negatives out of the 53 positive identified by the Thallium SPECT. That is, the ECG indicated 41% false negatives as compared to the Thallium SPECT results. Moreover, if the 11 ambiguous results presented in the middle row of the left-hand column were to be interpreted as negatives, the percentage of false reading would rise to 62%, as compared to the Thallium SPECT positive reading. Clearly this should not be tolerated, since about half of the patients identified by the Thallium SPECT to have a life threatening condition would have been told that they are healthy if tested only by the ECG method.

A comparison of the results of FIG. 14 with those of FIG. 17 clearly shows the superiority of the novel technique as compared, for example, to the ECG technique. However, the present invention also provides many important advantages even over the Thallium SPECT technique (as well as other known techniques), in its extreme simplicity, the inexpensive equipment required, the non-invasiveness of the procedure, and especially in the immediacy of the test results. The latter advantage is particularly important since it permits a test to be interrupted immediately if the onset of myocardial ischemia is detected, thereby reducing a life-threatening risk to the patient.

Figure 18:
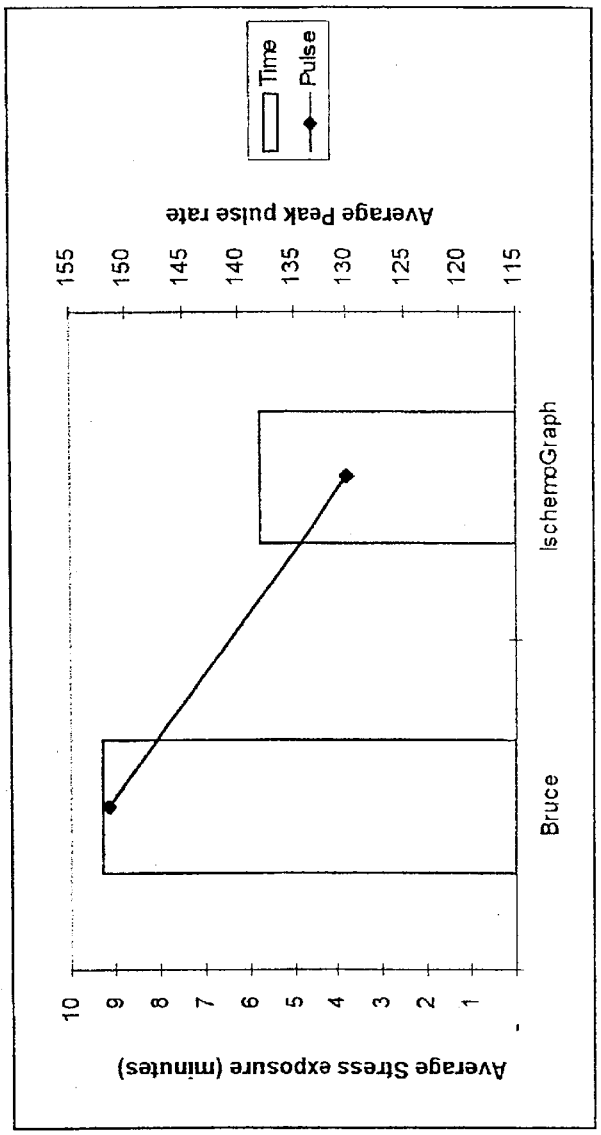

FIG. 18 more particularly illustrates certain of the advantages of the inventive technique, as investigated with respect to 25 patients. According to the data presented in FIG. 18, the mean time of a positive detection using the novel method of the present invention was shorter by over 40% (less than six minutes) as compared to the over nine minutes required by the conventional Bruce stress protocol.

This is an important advantage since, as noted above, it allows early termination of the test to reduce exposure to risk. Moreover, the data also shows that the inventive technique on average requires a 14% lower pulse rate than the stress Bruce protocol. This also provides a reduction in exposure to risk to the patient during the test. Finally it is to be noted that since the Bruce protocol is one of progressively increasing work load, the later stages of the test are the most dangerous and may be avoided using the inventive apparatus.

Figure 19:
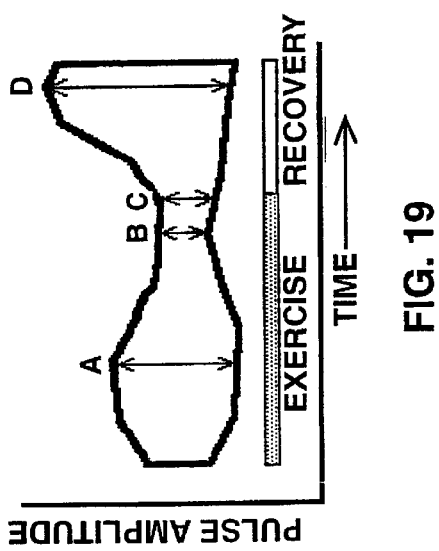
Figure 20:
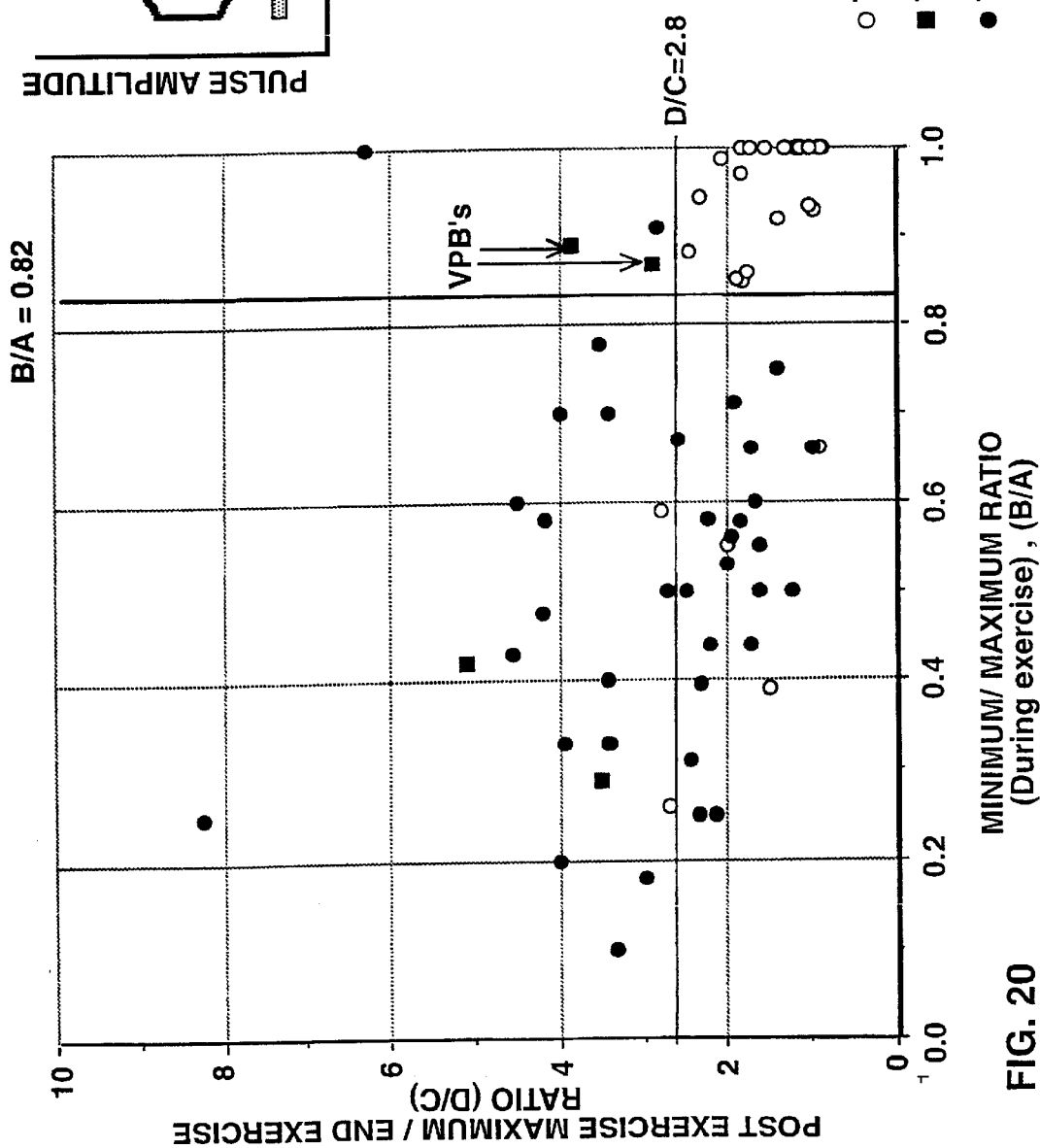

In the above-described tests, the decline in the output signal amplitude during the exercising period was used as the index of myocardial ischemia. Other aspects of the output signal-time course could also be used for providing valuable information. One particularly important example is the relative size and shape of the signal change during the post-exercise or recovery period. Thus, FIG. 19 illustrates the changes in the output signal amplitude during the exercise and recovery period, whereas FIG. 20 illustrates the relation of the post-exercise maximum/minimum (D/C) as compared to the minimum/maximum ratio during exercise (B/A).

In these tests, an indication of myocardial ischemia was determined when the ratio B/A dropped to 0.82 or below (i.e., a decline of 18% or more) during exercise, or the ratio D/C reached or exceeded 2.8 (i.e., a rise of 2.8 times or more) during the recovery period. Thus, the graph of FIG. 20 is divided into four quadrants, defined by the crosslines B/A=0.82 and D/C=2.8, wherein patients falling within the lower right quadrant are considered negative. As can be understood from the above, the sensitivity of the system can be changed by changing the "cut-off" values of the ratios, so as to move one or both cross-lines of FIG. 20. It is also to be understood that the exercise end point in terms of patient age related maximal heart rate will affect the values of the critical criteria.

It will be appreciated that the above-described technique may also be used in combination with one or more of the presently known techniques for indicating myocardial ischemia in order to improve the overall results. Particularly, the present invention can be used for initial screening conveniently and inexpensively done at the doctor's office. The doctor may then wish to confirm a positive result by having the patient undergo a second test of some type or undergo coronary angiography.

Monitoring Sleeping Conditions

As noted above, the present invention provides an advantageous non-invasive procedure for detecting a physiological state or medical condition. While most of the above discussion focuses on detecting myocardial ischemia, other physiological dysfunction can be detected using the inventive method and apparatus. For example, the present inventors have demonstrated that the above-described method and apparatus can be used for monitoring various sleeping conditions of a subject, particularly the rapid eye movement (REM) sleep stage and sleep apnea syndrome (SAS), as well as nocturnal myocardial ischemia.

Clinical Studies

The inventive apparatus has been tested on patients in a sleep clinic. REM episodes were depicted by the inventive apparatus characterized by reduction in the peak to trough amplitude of the pulse waves.

It is known that during REM, autonomic nervous regulation is disturbed. However, the relationship between REM and peripheral vasoconstriction is not presently clear. The peripheral vasoconstriction that was clinically linked to REM by the present inventors could be due to sympathetic hyperactivity, or alternatively, if coronary artery disease is present, due to the myocardial ischemia.

Episodes of sleep apnea were also recorded by the inventive Ischemograph. However, in some of these recordings there was an association between the gradual reduction of oxygen saturation monitored by the pulse oximeter and the gradual reduction of the Ischemographic pulse waves. Since general hypoxemia results in reduced oxygen supply to the myocardium this is, in fact, equivalent in effect to reduced normally saturated blood supply to the myocardium due to coronary artery disease or valvular heart diseases.

FIGS. 21a and 21c illustrate a so called "hypnogram" indicating the onset and duration of sleep stages including REM. When using the above-described inventive apparatus on a sleeping subject, it was seen that during every episode of REM stage sleep, the output signal from the apparatus fell in an abrupt and pronounced manner (See FIG. 21b). The heavy lines on the uppermost trace (FIG. 21a) are the REM period. Note the tight temporal link between REM and the Ischemographic signal's decline (shown in the middle trace, FIG. 21b).

Figure 22:
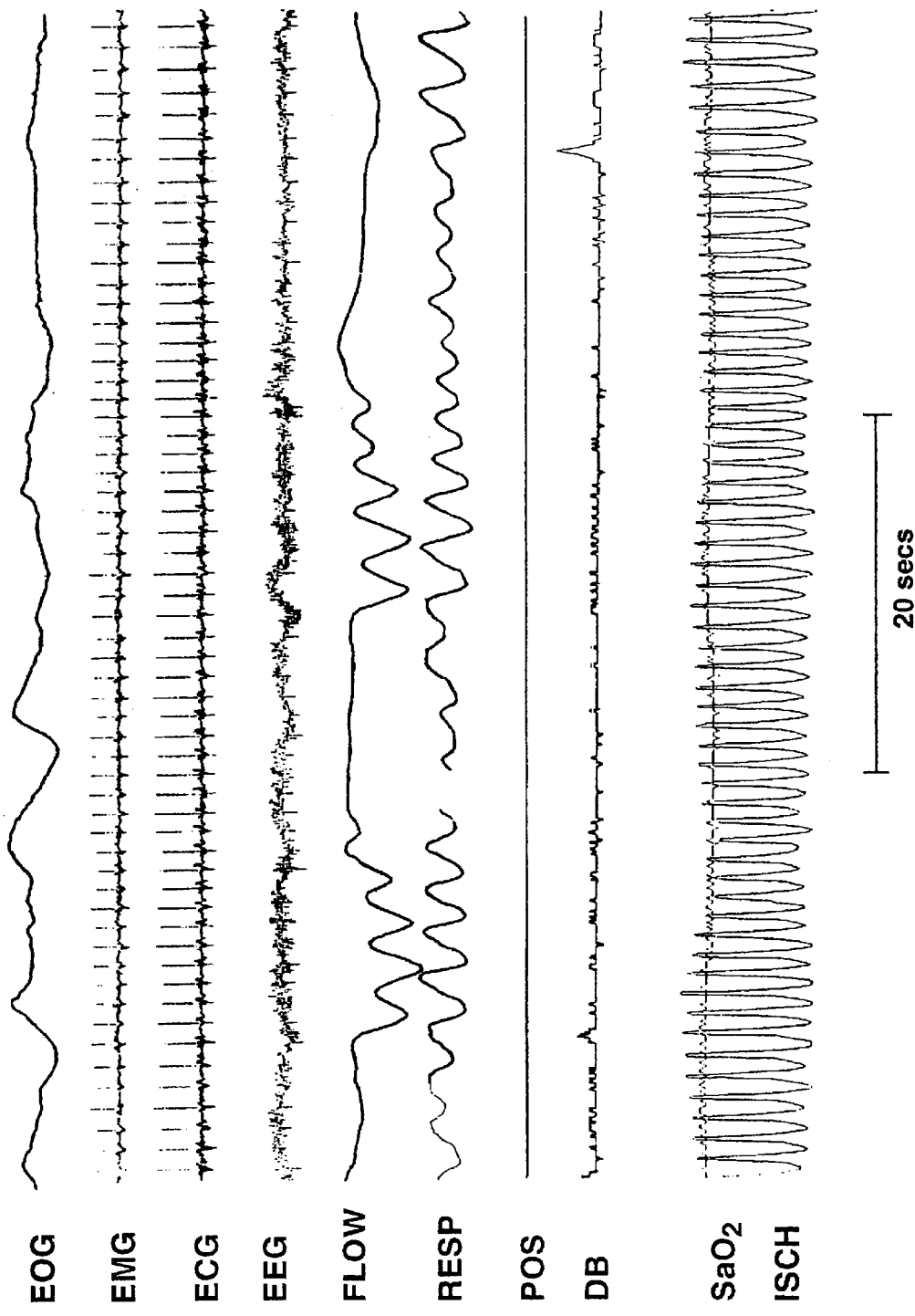

FIG. 22 is a segment of a standard polysomnographic recording during non-REM sleep, wherein it will be seen that each episode of apnea appears when the flow signal is flat. As shown in FIG. 22, with each episode of apnea, the output signal from the IschemoGraph (labeled ISCH) shows a repeated characteristic pattern of cyclic increases and decreases, following the time-course of oxygen saturation ($SaO_2$).

Thus, as shown in FIG. 22, there appears to be an association between the gradual reduction of oxygen saturation monitored by the pulse oximeter, and the gradual reduction of the output signals produced by the apparatus of the present invention. Since general hypoxemia results in reduced oxygen supply to the myocardium, this is, in fact, equivalent in effect to reduced normally saturated blood supply to the myocardium due to coronary artery disease or valvular heart disease.

Continuous non-invasive Blood Pressure Measurements

As mentioned above, with certain modifications and using a novel calibration procedure, the inventive method and apparatus may be used for the continuous non-invasive monitoring of blood pressure. Generally, the finger probe is used to detect pulsatile volume changes of the finger, caused by the pumping action of the heart. That is, the heart pumping action is detected by sensing pulsatile arterial blood volume changes in the finger.

As described above, the pressurized membrane is used to exert a static pressure field on the measured phalanx. The consequent slight encroachment of the arterial vasculature (unloading wall tension) results in amplification of the desired signals of the pulse waves. Also, the inventive feature of preventing venous pooling increases the accuracy and robustness of the blood pressure measurements, regardless of the actual sensor used, i.e., sensing volume changes, optical density changes, etc.

It will thus be seen that, while the ordinary plethysmography measures the volume changes of the entire studied mass, the present invention produces measurements which are specifically related to the pulsatile volume changes of only the arterial network of the studied part of the finger.

Unlike the existing methods of finger plethysmography, which are either in the form of a pressurized cuff or an unpressurized cap fitted to the fingertip, the present probe is in the form of a pressurized cap which encloses the entire fingertip. The conventional cap-shaped probes are unable to apply pressure without tending to forcibly expel the fingertip from within the probe. On the other hand, while cuffs are able to apply pressure without expelling the finger, they generate venous congestion distal to the cuff. The thimble-shaped pressure probe of the invention is devoid of these drawbacks. Firstly, the pressure in the cap preferably matches that of the tourniquet, thus preventing the distention of the venous vasculature. Secondly, means, such as the elastic strings (FIG. 1), the partitioning of the compartments (FIG. 2), or the restraining bar (FIG. 7), are provided to avoid the expulsion of the finger. The membranes are flexible, and are therefore able to adapt to the entire surface of the fingertip, including its extreme end.

Figure 23:
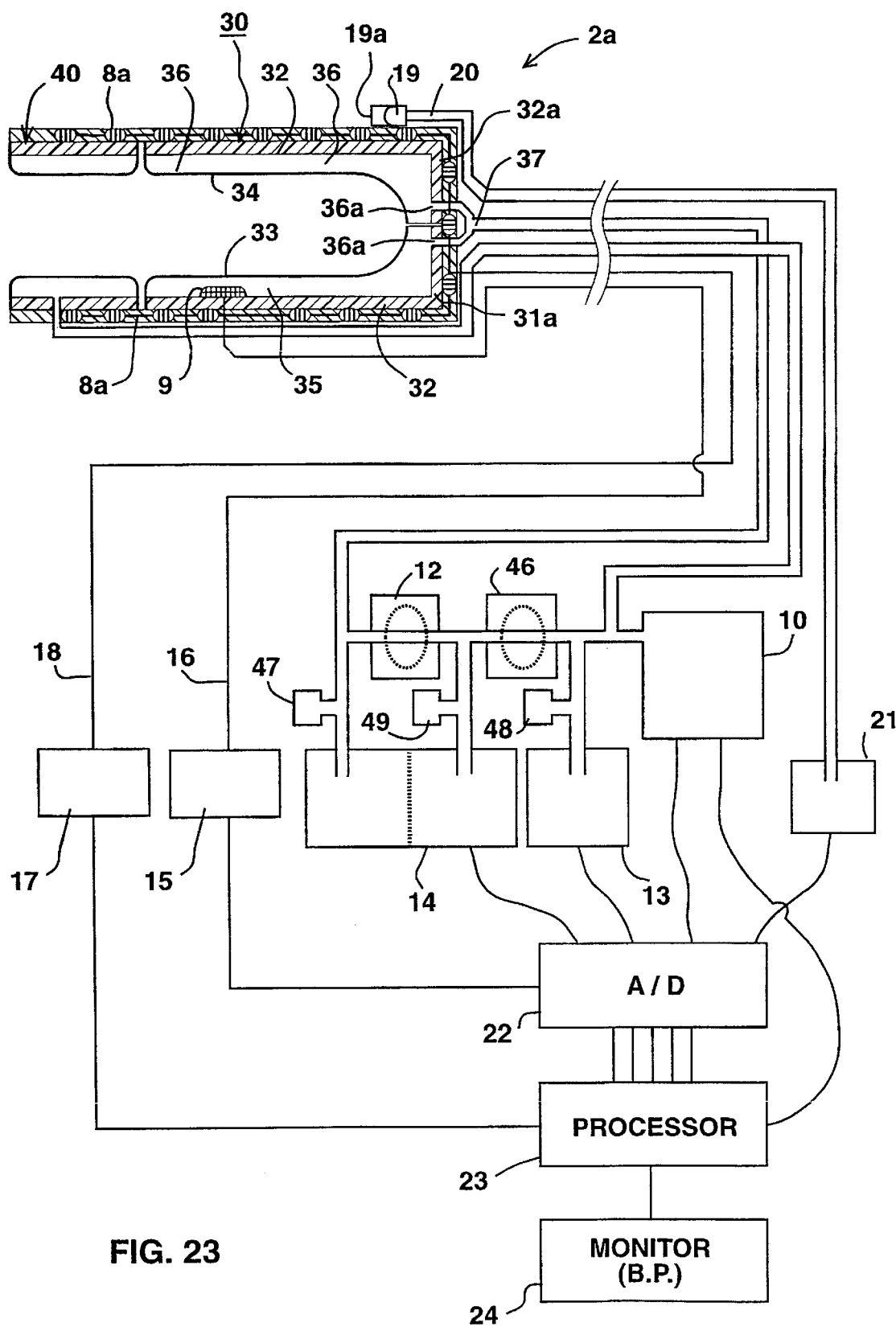
FIG. 23 depicts an embodiment of the apparatus of the present invention configured for continuous blood pressure measurements.

FIG. 23 depicts the finger probe 2a modified for continuous blood pressure measurements. It should be noted that any of the probes depicted in FIGS. 1–9 can be modified according to the description provided below. Specifically, as shown in FIG. 23, an electrical heater winding 8 protected by an outer thermal insulating layer 8a is applied around the outer surface of casing 30 for heating the subject's finger within the tubular membranes 33 and 34 to a pre-determined temperature, preferably 38–40° C. A thermistor 9 on the inner surface of the casing controls the electrical heater in order to maintain that temperature, so as to dilate the blood vessels in the finger.

Specifically, for the purpose of blood pressure measurements, the absolute value of the pulse wave relative to a zero baseline is of interest. As will be described in more detail below, these values are analyzed in terms of the patient's finger's vascular volume verses pressure relationship. Therefore, it is advantageous to cancel or avoid volume changes caused by any effects other than the heart's pumping action. To that effect, the finger is heated so that the arteries are maximally dilated to freely accommodate changes caused by the pulse wave thus effectively eliminating peripheral vasoconstriction at the measurement site. That is, the arteries' musculature (vascular smooth muscle) is maximally relaxed to minimize the resistance, so that the arteries behave in a passive manner, and exhibit no active tension.

As shown in FIG. 23 the electrical heater winding 8 is supplied with electrical power from a supply circuit 15 by wires 16. The temperature inside chambers 35 and 36 is regulated to the predetermined value, 38–40° C., by a controller 17 connected to thermistor 9 via electrical wires 18.

Additionally, since the absolute value of the signal is of interest, in FIG. 23 the high pass filter is removed. This allows determination of the absolute values of the peaks, troughs, and values in between. However, in order to provide an accurate blood pressure reading and indeed to effect the calibration procedure, one must also account for hydrostatic pressure differences relative to heart level, which can be very substantial. For a man of average height the difference is about 120 mmHg. Accordingly, the inventive apparatus was further modified to include novel means to gauge the hydrostatic pressure levels which are then used in a novel manner to calibrate the inventive apparatus.

For that purpose, the volume measuring apparatus illustrated in FIG. 23 further includes a sensor 19 for sensing the vertical position of the finger probe with respect to a reference point. This information is used during the calibration stage for converting the measured changes in finger volume to measurements of blood pressure. The sensor 19 is also used in the normal operation stage, for producing more precise measurements in situations where the subject's finger (or toe) changes its vertical position with respect to the subject's heart, e.g., as may occur when exercising.

In the embodiment exemplified in FIG. 23, the vertical position sensor 19 is in the form of a liquid (preferably water) filled housing closed at one end by a flexible membrane 19a and connected at its opposite end via a water filled tube 20 to a pressure transducer 21. Transducer 21 thus produces an electrical output corresponding to the vertical position of the water filled casing 19, and thereby of the finger probe 2a, with respect to the subject's heart level.

As noted above, arterial blood volume can be detected by various methods in addition to or instead of pneumatically. Therefore, while the system depicted in FIG. 23 pneumatically senses volume changes, other sensors can be used, such as the light source/receiver 100/101 depicted in FIG. 11. Also, it should be appreciated that the pressure cuff 40 can be eliminated and a probe having a membrane structure similar to that depicted in FIG. 1 can be used instead.

Calibration Procedure

Before the inventive apparatus is used for measuring blood pressure, it must first be calibrated to convert the measurement of volume changes to blood pressure. For this purpose, the subject raises and lowers the respective hand to produce a continuous series of hydrostatic pressures representing the vertical position of the subject's finger with respect to the heart level. These are added to the subject's arterial pressure, and both act against the initially applied counter-pressure (preferably 70 mm Hg) while the changes in volume in the subject's finger are measured by the changes in pressure in the expansible chambers of the finger probe.

At the beginning of the calibration procedure, the two valves 12 and 46 are opened, and the two chambers 35 and 36 of the cap 30 as well as chamber 43 of the pressure cuff 40, are deflated. This permits the subject to insert the finger through the annular membrane 43 of cuff 40, and between membranes 33 and 34 of the end cap 30. The three chambers are then inflated to the initial pressure of about 70 mm Hg, and the two valves 12 and 46 are closed. Heater 8 is then energized to heat the subject's finger to a temperature of 38–40° C., which temperature is maintained by thermistor 9 and temperature controller 17.

As mentioned above, heating the subject's finger to 38–40° C. maximally dilates the blood vessels in the subject's finger. The pressure of 70 mm Hg applied to the three chambers 35, 36, 42 represents the hydrostatic pressure in the veins of the subject's finger when the hand is completely lowered, plus a residual venous pressure of about 15 mm Hg representing the venous pressure at heart level, plus an added safety margin.

The subject gradually lifts the hand with the end cap 30 and cuff 40 to a maximum height above heart level, gradually lowers the hand to the lowest level below the heart, and lifts the hand back to the highest level above the heart. The vertical displacements of the end cap 30 are sensed by sensor 19 and are measured by transducer 21 which produces an output representing the hydrostatic pressure in each vertical position of the subject's finger with respect to the heart. The continuous changes in the pulsatile volume of the subject's finger accompanying the blood pressure waves are translated to changes in pressure in chambers 35, 36, and are measured by transducer 14. Transducers 21 and 14 may output their measurements via a wired or wireless transmission. The outputs of the two transducers 21 and 14 are converted to digital form by A/D converter 22 and are applied to CPU 23 for processing. The hydrostatic pressure values are continuously subtracted from the fixed counter pressure to give the effective applied pressure (Pappl), which is the value by which intra-arterial pressure is changed from its heart level value as the finger is shifted.

During the raising and lowering of the hand, the voltage output of the pulse signal is also entered into the CPU. The peak (systolic) and trough (diastolic) points of each pulse are identified together with their corresponding Pappl values. The data pairs of systolic values and their corresponding Pappl values are analyzed to give a regression equation called the systolic function. Likewise, the set of diastolic values are analyzed to give the relationship between the diastolic values and the corresponding Pappl, referred to as the diastolic function.

The diastolic function is then tested to determine the point at which the terminal portion of the individual pulse waves ceases to be flat, which occurs because Pappl is greater than the internal arterial pressure and the arteries are forced to collapse to their minimal volume. This is the diastolic pressure.

Once the patients' diastolic blood pressure is known, the effective arterial pressure at every level of vertical displacement of the diastolic function can then be accurately calculated by adding the hydrostatic pressure value to the diastolic pressure value. If flattening of the diastolic function does not occur when the arm is fully raised, then extra external pressure is added until it does.

Systolic pressure is calculated by identifying the first sign of pulse reappearance during lowering of the hand if systolic pressure was lower than the external pressure and the reduction in arterial pressure due to raising of the hand. If this is not the case, then systolic pressure is calculated by identifying two points at which diastolic and systolic volume signals are equal and measuring the hydrostatic pressure differences between them and adding this to the diastolic value. This is best done at a point slightly beyond where the diastolic function has passed from the flattened phase. The relationship for determining pressure as a function of the pulse signal voltage is then subsequently used to provide a calibrated pressure scale for converting pulse signals into pressure data.

It should be appreciated from the above description that the inventive feature of preventing venous pooling is particularly beneficial during the calibration process. That is, for proper calibration, the pressure changes should correspond only to the arterial volume changes. However, if venous pooling is not prevented, blood may accumulate in the finger and the pressure would cease to be a function of arterial volume changes only.

Operation for Blood Pressure Measurements

The following is an explanation of how the apparatus illustrated in FIG. 23 is used to measure directly changes (as a function of time) in volume of the subject's finger accompanying blood pressure waves resulting from the subject's heartbeat, and to convert such measurements to blood pressure via a calibration procedure described below.

For measuring finger volume changes, the subject's finger is inserted into the tubular socket defined by the finger probe 2a, such that the end cap 30 encloses the most distal phalange of the subject's finger, and the cuff 40 covers the adjacent phalange, as shown in FIG. 4b. The chambers are then pressurized and the electrical heater 8 is energized to heat the finger to a temperature of about 38–40° C. This temperature is maintained by temperature controller 17 and produces maximal dilation of the arterial blood vessels in the subject's finger and thereby maintain a steady state of minimal resistance to blood flow during the subsequent measurements. It also serves to maintain the gas temperature constant. The membranes are pressurized by source 10 to a predetermined pressure sufficient to substantially prevent pooling of venous blood and uncontrolled venous backflow, and also to partially unload the wall tension of, but not to occlude, the finger arteries when the finger is at heart level. This predetermined pressure is preferably about 70 mm Hg in this described example.

The expansion and contraction of the arterial blood vessels in the finger resulting from the blood pressure waves produced by the subject's heartbeat will contract and expand the pressurized chambers 35 and 36 of the finger probe 2a. The resulting pressure changes within these chambers are sensed by the pressure transducer 14, converted to digital information by A/D converter 22, processed in processor 23, and displayed on monitor 24 in the form of continuous blood pressure measurements.

The use of annular pressure cuff 40 is advantageous in that it extends the pressure field applied by the end cap 30 beyond the site of measuring the finger volume changes, such that the boundary of the actual measurement site is within the fully developed pressure region.

Exemplary Data

The output of the system can be displayed on an appropriate monitor with appropriate display of selected values such as the average systolic, diastolic, or mean pressure over a predetermined time. In addition to the displayed signal, the blood pressure versus time data can be sampled at a predetermined rate and stored in the computer memory for subsequent retrieval.

Figure 24:
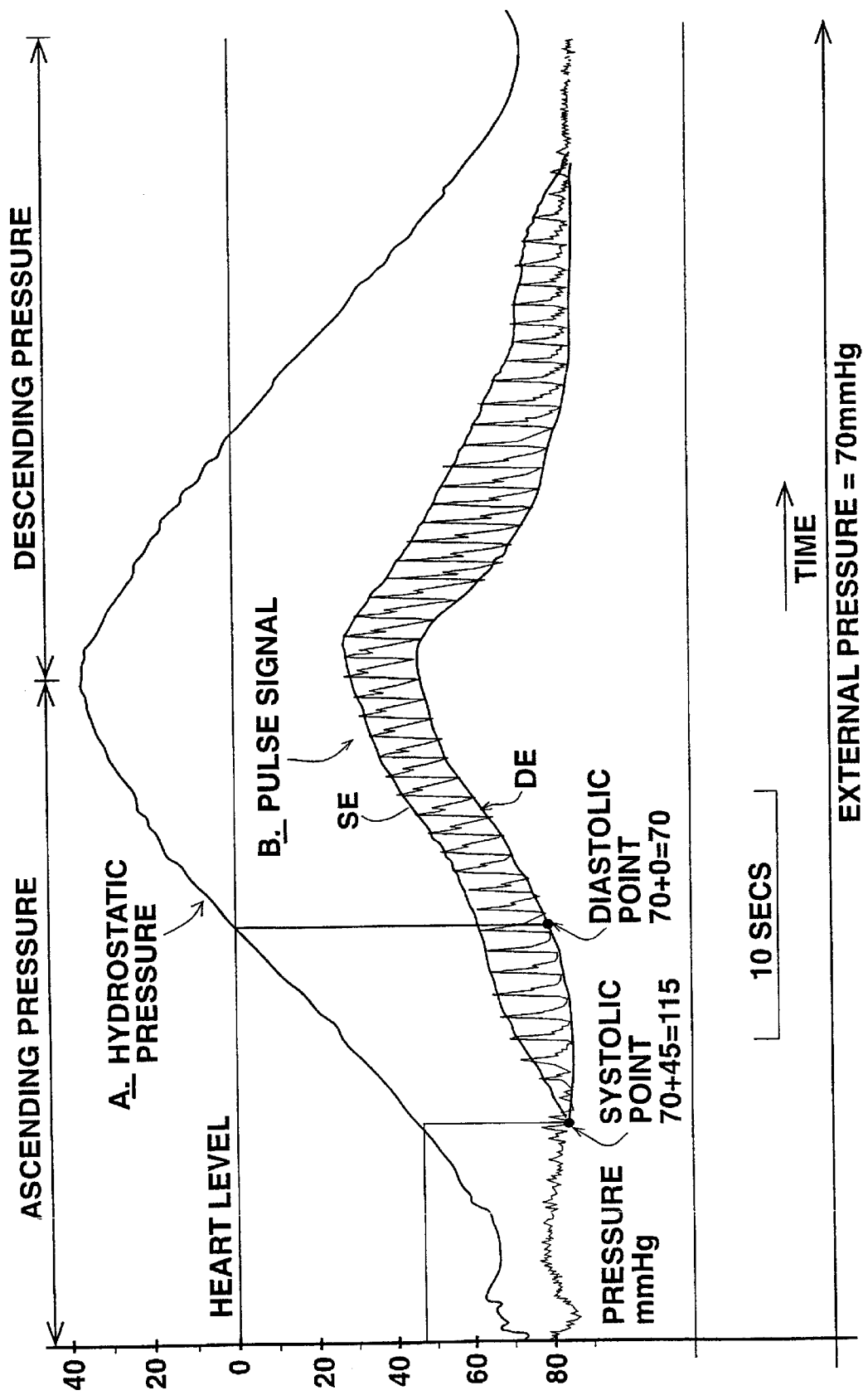
FIGS. 24 and 25 depict clinical data curves obtained during calibration of the inventive apparatus exemplified in FIG. 23.

In FIG. 24, curve A represents the changes in hydrostatic pressure induced by first lowering and then raising the subject's hand as sensed by elevation sensor 19 and transducer 21. It will thus be seen from curve A that the hydrostatic pressure is at a maximum negative value when the subject's finger is at the highest position, gradually increases during the lowering of the hand to be "zero" at heart level, and gradually increases thereafter to its maximum positive value when the subject's finger is at the lowermost position. A reversed sequence of changes in the hydrostatic pressure is produced as the hand is raised back to its uppermost position. Preferably, the procedure is repeated a second time and the average values are used.

Curve B represents the pressure outputs of the chambers 35, 36, caused by the changes in volume of the subject's finger within the end cap 30, and thereby the changes in volume of the subject's finger accompanying the blood pressure waves resulting from the subject's heartbeat.

Thus, as shown by curve B, when the subject's finger is at the highest elevation, the highly-negative hydrostatic pressure (curve A) together with the subject's arterial pressure are not sufficient to overcome the 70 mm counter-pressure, so that the finger arteries are occluded during both systole and diastole. As the subject lowers the finger, the hydrostatic pressure (curve A) becomes less negative such that the arteries open first at the pressure peaks (systole), and then open at the pressure troughs (diastole). Thus, curve B defines a systolic envelope SE at the peaks, and a diastolic envelope DE at the troughs. The diastolic end point DP is determined to be the point at which the terminal portion of the individual pulse waves ceases to be flattened, i.e. the diastolic signal terminates as sharply as in the pulse waves recorded when the arm is more completely lowered. The systolic end point SP is that point at which the first traces of a pulse wave begin to appear upon lowering the arm. In both cases these events occur at about the time the respective envelopes SE and DE begin to rise. The systolic point SP can also be determined by identifying the two points at which the diastolic and systolic envelopes are equal in volume, adding to the diastolic pressure the pressure difference between the two envelopes at this point.

Figure 25:
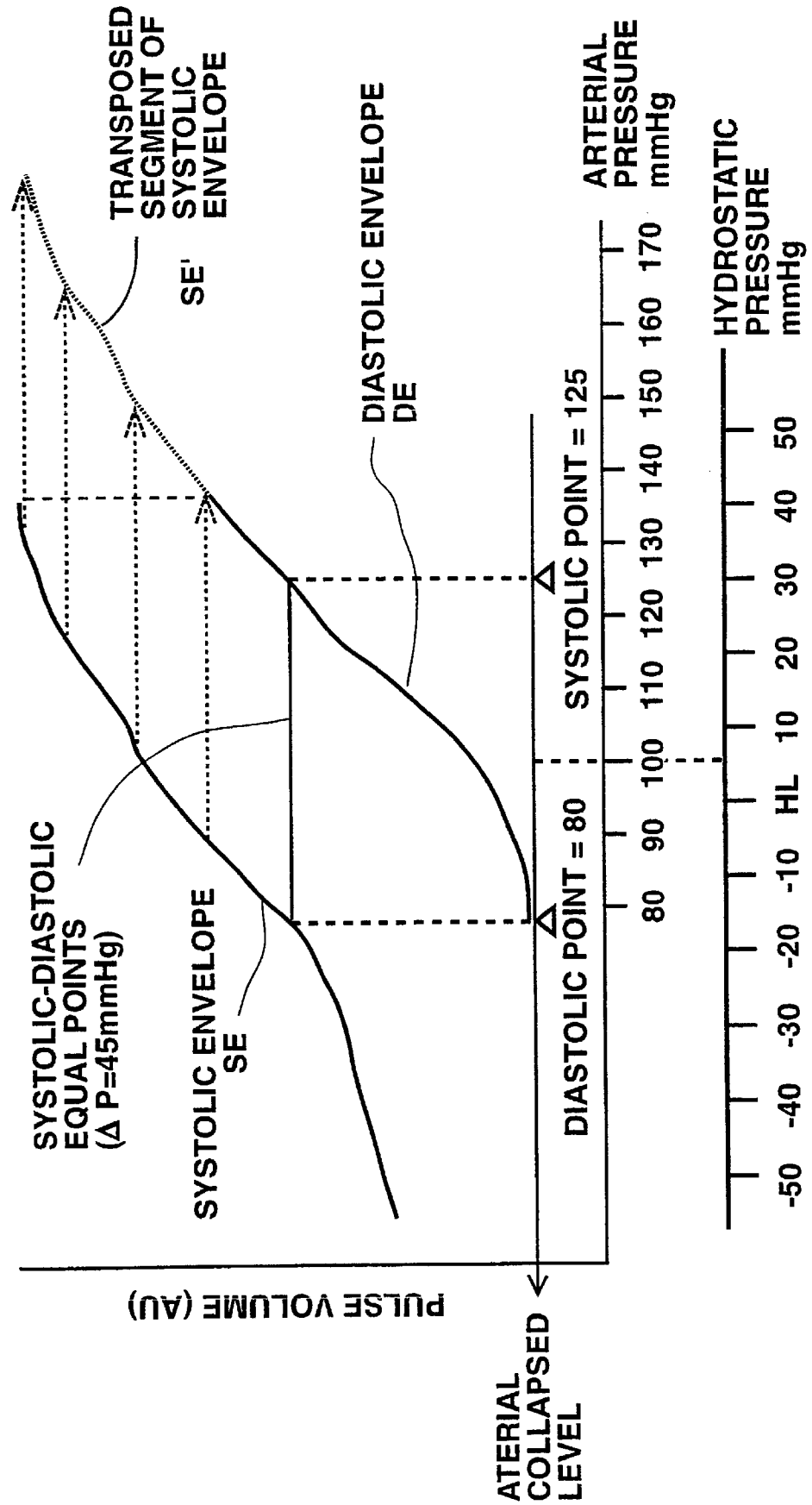

FIG. 25 illustrates, in another case, how the so-constructed systolic envelope SE and diastolic envelope DE may be used for converting volume changes as measured by chambers 35 and 36 to blood pressure of the subject. Thus, in FIG. 25, curve DE represents the portion of the diastolic envelope DE just as the artery begins to open during diastole. In this case, this diastolic point is when the finger is below the heart level at about 13 cm., so that the hydrostatic pressure is −10 mm Hg. Since the applied external pressure is 70 mm, the diastolic pressure in this case is 70-(−10), or 80 mm Hg.

In the example illustrated in FIG. 24, the systolic point at which the artery begins to open during systole is at 115 mm Hg (i.e., 70 mm due to the external pressure plus the hydrostatic pressure of −45 mm). In FIG. 25, the portion of the systolic envelope SE above the diastolic point must be increased by 45 mm, as shown at SE' in FIG. 25, such that the determined systolic end point is 80+45, or 125 mm Hg.

Once the apparatus has been calibrated as described above, the curve illustrated in FIG. 25 may be retained in the memory of the processor 23 (e.g., as by look-up tables or by a polynomial equation), such that the measured volumes are automatically converted to arterial pressure before being displayed in the monitor 24 as a function of time.

It will thus be seen that once the apparatus has been calibrated as described above, the measured changes in volume of the blood flow through the subject's finger accompanying the blood pressure waves will then be transformed and displayed in monitor 24 as complete pressure pulses enabling the viewer to continuously monitor, in a non-invasive manner, the continuous blood pressure wave forms of the subject, including the systolic and diastolic pressures.

During ongoing continuous blood pressure measurement, the vertical displacement of the measurement site with respect to heart level continues to be monitored. The hydrostatic pressure deviation from the heart level is continuously subtracted from the blood pressure data such that the actual results are corrected for hydrostatic pressure variations and blood pressure is displayed in the corrected form.

Comparative Data

Figure 26:
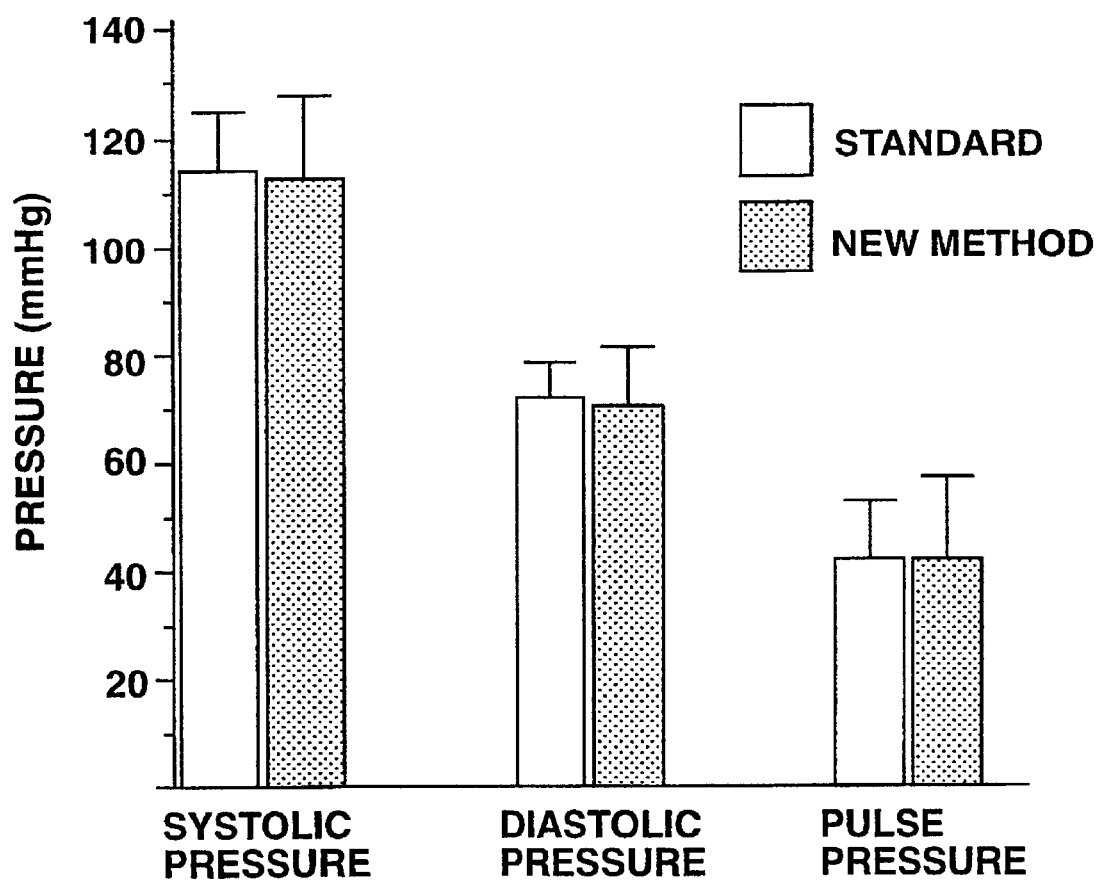
FIGS. 26 and 27 are data charts comparing the results obtained when using the blood pressure measuring technique of the present invention as compared to the standard sphygmomanometric technique.
Figure 27:
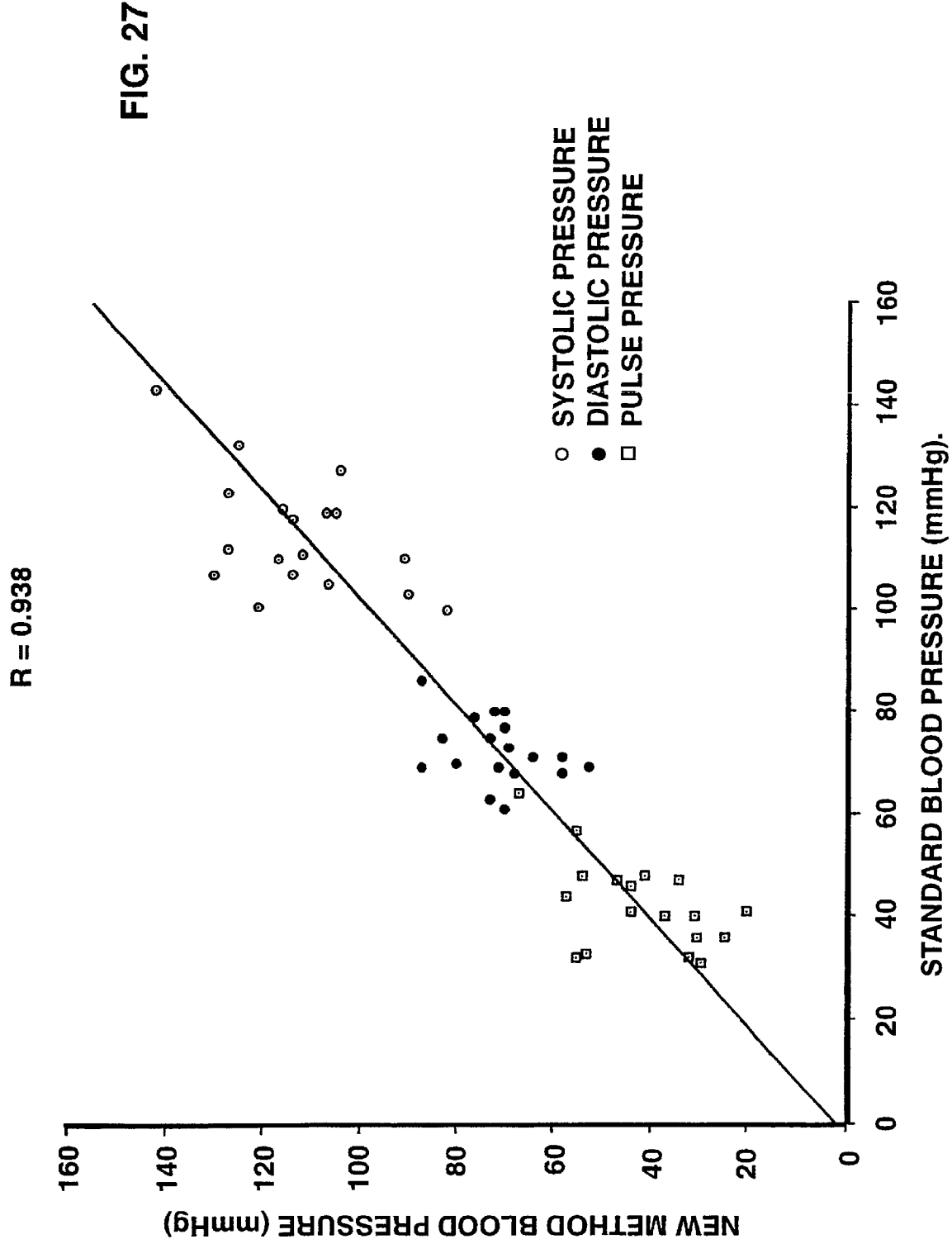

FIGS. 26 and 27 present comparative data comparing the results produced by the novel technique, particularly as described above with respect to FIGS. 23–25, with the standard sphygmomanometric technique for measuring blood pressure. The reported systolic and diastolic values of the novel device were the respective values determined from the previously described calibration technique in which systolic and diastolic values are determined. Values given are means of two determinations.

Standard blood pressure values (mean of three determinations) were measured either immediately before or immediately after the measurements taken with the inventive apparatus. For both methods data were recorded from the same arm. Since the object was to validate systolic and diastolic end point determined with the inventive method, it was decided to base the comparison against standard non-invasive blood pressure measurements rather than against intraarterial measurements which are technically difficult to perform. The data presented in FIGS. 26 and 27 resulted from a study made on 18 subjects (12 males, 6 females) all of normal weight, aged 23–60, and normotensive (systolic blood pressure 100–143, diastolic blood pressure 61–86, pulse pressure 31–64). FIG. 26 includes bar graphs of mean and SD (standard deviation) of systolic, diastolic and pulse pressure measurements made according to the present invention. While the standard deviation according to the invention is somewhat higher than that of the comparative standard method, the actual measurements are practically in agreement. Variance with the new method may be greater since the standard method is known to under-estimate beat to beat blood pressure changes due to its prolonged gradual pressure release.

FIG. 27 is a scattergraph of the data produced comparing the novel technique with the standard technique. Again, as can be seen from the graph, the data follows a linear relationship between the comparative standard method and the inventive method. The correlation coefficient (R=0.938) is very highly significant.

Although the invention has been described and shown in terms of a preferred embodiments thereof and experimental set ups, it will be understood by those skilled in the art that changes in form and detail may be made therein without departing from the spirit and scope of the invention as defined in the appended claims.

What is claimed is:

1. A method for the non-invasive detection of a change in physiological condition of a patient, comprising steps of monitoring changes in peripheral arterial tone and determining that a change in the physiological condition of the patient has occurred when a specific change in the peripheral arterial tone has been detected.

2. The method of claim 1, wherein said physiological condition is one of myocardial ischemia, on-set of REM sleep state, and sleep apnea.

3. The method of claim 1, further comprising a step of applying a pressure to the measuring site, said pressure being sufficient to (a) substantially prevent venous pooling at said measuring site (b) substantially prevent uncontrolled venous backflow at said measuring site and (c) partially unload the wall tension of, but not to occlude, the arteries at said measuring site when the measuring site is at heart level or below.

4. The method of claim 1, wherein the step of monitoring changes in peripheral arterial tone comprises monitoring changes in blood flow of skin arteries.

5. The method of claim 1, wherein the step of monitoring changes in peripheral arterial tone comprises monitoring changes in blood flow of a digit's arteries.

6. An apparatus for detecting a change in a physical condition of a patient, comprising:
a probe to be applied to a digit of the patient, said probe sensing the peripheral arterial tone of the digit; and
a processor receiving signals from said probe and providing an output indicating changes in the peripheral arterial tone of said digit, thereby indicating a physiological state or medical condition of the patient.

7. The apparatus of claim 6, wherein said probe comprises a membrane for applying a pressure sufficient to (a) substantially prevent venous pooling in said digit and (b) partially unload the wall tension of, but not to occlude, the arteries in said digit.

8. The apparatus of claim 7, wherein said apparatus further comprises a sensor for monitoring changes in blood volume in said digit.

9. The device of claim 6, wherein said probe further includes a pressure cuff.

10. A probe to be applied to a digit for detecting peripheral vasoconstriction, said probe comprising:
a membrane for applying a pressure sufficient to partially unload the wall tension of, but not to occlude, the arteries in said digit; and
means for substantially preventing venous pooling in said digit.

11. The probe of claim 10, further comprising a sensor for monitoring changes in blood volume in said digit.

12. A method for non-invasive detection of physiological dysfunction of a patient, comprising:
applying a static pressure field around the distal end of a digit of the subject, including the extreme digit tip, which static pressure field is sufficient to (a) substantially prevent venous pooling in said distal end, (b) substantially prevent uncontrolled venous backflow in said distal end, and (c) partially unload the wall tension of, but not to occlude, the arteries in said distal end when the digit is at heart level; and
measuring changes in peripheral arterial tone and related volume changes in said distal end of the digit accompanying the arterial pulse waves.

13. The method according to claim 12, wherein said volume-related changes are measured by measuring changes in volume in said distal end.

14. The method according to claim 12, wherein said volume-related changes are measured by measuring changes in optical density in said distal end.

15. The method according to any one of claims 12–14, wherein said measured changes are monitored for indicating the existence of myocardial ischemia in the patient.

16. The method according to any one of claims 12–14, wherein said measured changes are monitored for indicating at least one of onset and duration of rapid eye movement (REM) sleep, and sleep apnea.

17. The method according to any one of claims 12–14, wherein said static pressure field is in the range of approximately 30 mm Hg to about 10% above the patient's diastolic pressure.

18. The method according to any one of claims 14, wherein said static pressure field is applied around a portion of the finger proximal to, and including, the finger's extreme tip.

19. The method according to claim 18, wherein said static pressure field is applied by a thimble-shaped probe including an end cap enclosing at least the most distal phalange, and a contiguous annular cuff.

20. The method according to any one of claims 12–14, wherein said static pressure field is 70 mmHg.

21. A probe for detecting changes in peripheral arterial tone, comprising:
a pressure applicator including an end cap for receiving, and for applying pressure to, the most distal phalange of a patient's digit, and a cuff for receiving, and for applying pressure to, the phalange of the patient's digit preceding the distal part of the digit;
said cuff acting as a venous tourniquet to prevent venous blood pooling in said digit, retrograde venous blood flow, and retrograde venous shock wave propagation into the distal part of the digit; and
said cap detecting pulsatile volume changes of the arteries in said most distal phalange, preventing venous pooling in said digit and partially unloading the wall tension of, but not occluding the arteries therein.

22. The probe of claim 21, further comprising a heating mechanism.

23. The probe of claim 22, further comprising a vertical displacement sensor.

24. The probe of claim 21, wherein said pressure compartment is defined by a deformable tubular membrane, and wherein said probe further comprises means for preventing said membrane from axial movement when pressurized, so as to avoid expelling a finger placed in the probe.

25. The probe of claim 24, wherein said deformable tubular membrane is divided into two sections at diametrically opposite sides of the finger.

26. The probe of claim 24, wherein said end cup is divided into a plurality of casing sections, each of said plurality of casing sections having a membrane section connected thereto, and wherein said plurality of casing sections are joined together to define said end cup.

27. The probe of claim 24, wherein said means for preventing said membrane from axial movement comprises a restrainer bar fixed to the casing and having a mid-portion received within the tubular membrane so as to restrain inward axial displacement of the membrane.

28. A method for calibrating a blood pressure measuring instrument, comprising the generation of a compliance curve of the measured arterial blood vessels by inducing and monitoring hydrostatic pressure changes within these blood vessels by changing the vertical position of a measurement site with respect to the heart and measuring corresponding volumes and other volume correlated features of such arterial blood vessels and then plotting such measured values and the induced hydrostatic pressure changes.

29. A method for measuring the arterial blood pressure of a subject, comprising:
heating the distal end of a digit of the subject's body to a predetermined temperature to maximally dilate the arterial blood vessels in said digit; and
measuring volume-related changes in said distal end of the digit accompanying blood pressure waves;
and converting said measured changes to arterial blood pressure.

30. The method according to claim 29, wherein a static pressure field is applied around the distal end of the digit sufficient to substantially prevent pooling of venous blood and to partially unload the wall tension of, but not to occlude, the digit arteries when the digit is at heart level or below.

31. The method according to either of claims 29 or 30, wherein said measured changes are changes in optical density in said distal end of the digit accompanying blood pressure waves.

32. The method according to any one of claim 30 wherein said measured changes in the distal end of the digit are converted to arterial blood pressure by:
applying said static pressure field as a predetermined external counter-pressure to the digit;
vertically displacing the digit through a plurality of vertical positions with respect to the subject's heart;
measuring the hydrostatic pressure added to the subject's blood pressure by each vertical position of the subject's digit with respect to the subject's heart;
and utilizing said predetermined external counter-pressure and said hydrostatic pressure measurements for calibrating said measured changes in the outer end of the subject's digit in terms of the arterial blood pressure of the subject and for converting said measured changes to arterial blood pressure.

33. The method according to either of claims 29 or 30, wherein said measured changes are changes in volume in said distal end of the digit accompanying blood pressure waves.

34. A probe for measuring changes in peripheral arterial tone of a subject, comprising:
a rigid casing having an open end and a closed end;
a compliant membrane disposed inside said casing and hermetically connected to the open end of said casing;
a circular pressure band provided inside said casing and positioned to press said membrane against interior wall of said casing; and
a substantially U-shaped restraining bar disposed inside the casing and positioned against the membrane so as to prevent axial shifting of the membrane when inflated to avoid expelling of a finger placed therein.

35. The probe of claim 34, wherein said pressure band divides said membrane into two hermetically sealed pressure chambers.

36. The probe of claim 34, further comprising an optical sensor.

37. An apparatus for monitoring the arterial pulse waves of a subject, comprising:
a pressure applicator including a tubular socket for receiving a predetermined length of the distal end of a digit of the subject's body, including the extreme distal tip of the digit;
a pressure source for applying a static pressure field around the distal end, including the extreme distal tip, of the digit of the subject's body when received in said tubular socket, which static pressure field acts as a venous tourniquet to substantially prevent pooling of venous blood in the distal end of the digit, to prevent retrograde venous blood flow and erratic venous shock wave propagation into the distal part of the digit, which could produce artifacts at the measuring site, and to partially unload the wall tension of, but not to occlude, the arteries therein when the digit is at heart level; and,
a measuring device for measuring changes in said distal end of the digit associated with blood pressure waves.

38. The apparatus according to claim 37, wherein said measuring device measures changes in volume in said distal end of the digit associated with blood pressure waves.

39. The apparatus according to claim 37, wherein said measuring device measures changes in optical density in said distal end of the digit associated with blood pressure waves.

40. The apparatus according to any one of claims 37–39, wherein said pressure applicator applies a static pressure around the distal end of the digit which is extended in the proximal direction towards the subject's heart for a predetermined distance from the site at which said changes are measured.

41. The apparatus according to any one of claims 37–39, wherein said pressure applicator comprises:
a casing having a deformable tubular membrane mounted therein and defining a tubular chamber with said casing; and
a fluid pressure source for applying fluid pressure to said tubular chamber to cause the tubular membrane to deform according to changes in volume of blood flow through the subject's digit when received therein;
wherein said deformable tubular membrane is divided into a plurality of sections.

42. The apparatus according to claim 41, wherein said deformable tubular membrane is divided into two sections at diametrically opposite sides of the subject's digit when received therein.

43. The apparatus according to claim 41, wherein said casing is divided into a plurality of sections, one for each of said membrane sections, and joined together to define said outer tubular chamber with said membrane sections.

44. The apparatus according to claim 41, wherein said tubular membrane is divided into said plurality of sections by a restrainer bar affixed to the casing and having a mid-portion received within the tubular membrane so as to restrain the inward displacement of outer periphery of each membrane section during the application of said fluid pressure to said tubular chamber.

45. The apparatus according to claim 37, wherein said pressure source applies a static pressure field in the range of 30 mm Hg to about 70 mm Hg.

46. The apparatus according to claim 37, wherein said apparatus further includes a converter for converting said measured changes in said outer end of the digit to arterial blood pressure of the subject.

47. The apparatus according to claim 46, wherein said converter includes:
a measuring device for measuring hydrostatic pressure added to the subject's blood pressure when vertically displacing the digit through a plurality of vertical positions with respect to the subject's heart; and
a computer utilizing said static pressure field and said hydrostatic pressure measurements for calibrating said measured changes in the outer end of the subject's digit in terms of the arterial blood pressure of the subject, and for converting said measured changes to arterial blood pressure.

48. The apparatus according to claim 46, wherein said apparatus further includes a pre-heater for pre-heating said digit to a predetermined temperature to maximally dilate the arterial blood vessels in said digit.

49. The apparatus according to claim 37, wherein said pressure applicator is incorporated into at least one finger of a glove to be worn by the subject and to measure changes associated with blood pressure waves in the distal end of the finger of the subject's hand received within said finger of the glove.

50. The apparatus according to claim 37, wherein said pressure applicator applies a pressure of 70 mm Hg.

51. Apparatus for monitoring a hemodynamic condition of a subject, comprising:
   a tubular socket for receiving the distal end of a digit of the subject's body;
   a heater within said socket for heating the distal end of the digit of the subject's body to a predetermined temperature to maximally dilate the arterial blood vessels in said digit; and
   a measuring device for measuring changes in said distal end of the digit associated with blood pressure waves.

52. The apparatus according to claim 51, wherein said socket includes a pressure applicator for applying a static pressure field around the distal end of the digit sufficient to substantially prevent pooling of venous blood and to partially unload the wall tension of, but not to occlude, the digit's arteries when the digit is at heart level.

53. The apparatus according to either of claims 51 or 52, wherein said measuring device measures changes in volume in said distal part of the digit associated with blood pressure waves.

54. The apparatus according to either of claims 51 or 52, wherein said measuring device measures changes in optical density in said distal part of the digit associated with blood pressure waves.

55. Apparatus for detecting cardiopulmonary distress in a subject, comprising:
   a pressure applicator including a tubular socket for receiving a predetermined length of the distal end of a digit of the subject's body, including the extreme distal tip of the digit;
   a pressure source for applying a static pressure field around the distal end of said digit of the subject's body when received in said tubular socket, which static pressure field is sufficient to substantially prevent pooling of venous blood in the distal end of the digit and to partially unload the wall tension of, but not to occlude, the arteries therein when the digit is at heart level;
   a measuring device for measuring changes in said distal end of the digit associated with blood pressure waves;
   and an indicator for providing an indication of the existence of cardiopulmonary distress when said measured changes exceed a predetermined percentage as compared to a normal known condition of the subject when cardiopulmonary distress is not present.

56. Apparatus for monitoring a sleeping subject, comprising:
   a pressure applicator including a tubular socket for receiving a predetermined length of the distal end of a digit of the subject's body, including the extreme distal tip of the digit;
   a pressure source for applying a static pressure field around the distal end of the digit when received in said tubular socket, which the static pressure field is sufficient to substantially prevent pooling of venous blood in the distal end of the digit and to partially unload the wall tension of, but not to occlude, the arteries therein when the digit is at heart level;
   a measuring device for measuring changes in said distal end of the digit associated with blood pressure waves;
   and an indicator utilizing said measured changes for providing an indication of the sleeping condition of the subject.

57. The apparatus according to either of claims 55 or 56, wherein said measuring device measures changes in volume in said outer end of the digit associated with blood pressure waves.

58. The apparatus according to either of claims 55 or 56, wherein said measuring device measures changes in optical density in said outer end of the digit associated with blood pressure waves.

59. The apparatus according to any one of claims 55 or 56, wherein said pressure applicator applies a pressure in the range of 30 mm Hg to 70 mm Hg.

60. The apparatus according to any one of claims 55–56, wherein said pressure applicator applies a static pressure around the distal end of the digit which static pressure field is extended in the direction towards the subject's heart for a distance from the site at which said changes are measured.

61. The apparatus according to any one of claims 55–56, wherein said pressure applicator comprises a casing having a deformable tubular membrane mounted therein defining an outer tubular chamber with said casing, and said inner tubular socket for receiving said distal end of the subject's digit;
   said pressure source applying said static pressure field to said outer tubular chamber to cause the tubular membrane to deform according to changes in volume of the subject's digit, when received therein, associated with blood pressure waves;
   said deformable tubular membrane being divided into a plurality of sections around the subject's digit when received therein, each section including a central region and an outer periphery, the outer periphery of each section being restrained from inward displacement, such that the pressure within the outer tubular chamber inwardly displaces the central region of each membrane section to a greater degree than the outer periphery thereof, thereby causing said inwardly displaced central regions of the plurality of membrane sections to firmly clamp the device to the subject's digit against axial and rotary movement of the device with respect to the body extremity.

62. The apparatus according to claim 61, wherein said deformable tubular membrane is divided into two sections at diametrically opposite sides of the subject's digit when received therein.

63. The apparatus according to claim 61, wherein said casing is divided into a plurality of sections, one for each of said membrane sections, and joined together to define said outer tubular chamber with said membrane sections, each of said membrane sections being constituted of a substantially four sided membrane secured at its peripheral edges to the peripheral edges of its respective casing section.

64. The apparatus according to claim 61, wherein said tubular membrane is divided into said plurality of sections by a restrainer bar fixed to the casing and having a mid-portion received within the tubular membrane so as to restrain the inward displacement of the outer periphery of each membrane section during the application of said fluid pressure to said outer tubular chamber.

65. A method for non-invasive detection of a physiological condition of a patient, comprising:
   monitoring changes in peripheral pulsatile volume; and
   determining the physiological condition of the patient when a predetermined change in the peripheral pulsatile volume is detected.

66. A method as recited in claim 65, wherein the changes in peripheral pulsatile volume reflect changes in peripheral arterial tone.

67. The method of claim 1, wherein said monitoring step is performed continuously and/or in real time.

68. The apparatus of claim 6, wherein said probe is adapted to sense the peripheral arterial tone continuously and/or in real time.

* * * * *

UNITED STATES PATENT AND TRADEMARK OFFICE
CERTIFICATE OF CORRECTION

PATENT NO. : 6,319,205 B1
DATED : November 20, 2001
INVENTOR(S) : Daniel A. Goor et al.

It is certified that error appears in the above-identified patent and that said Letters Patent is hereby corrected as shown below:

Title page,
Item [75], Inventors, change the first and second named inventors to read as follows:
-- Daniel A. Goor, Tel Aviv; Robert P. Schnall, Kiryat Bialik --
Item [57], ABSTRACT, change the penultimate line thereof to read as follows:
-- The apparatus includes a finger probe (2), in the form of a tube (30) accommodating the patient's finger, which is designed to apply pressure, and a contiguous pressure cuff (40) which extends the boundary of the pressure field. --

Drawings,
Replace Fig. 2a on Sheet 2 of the drawings with the following figure:

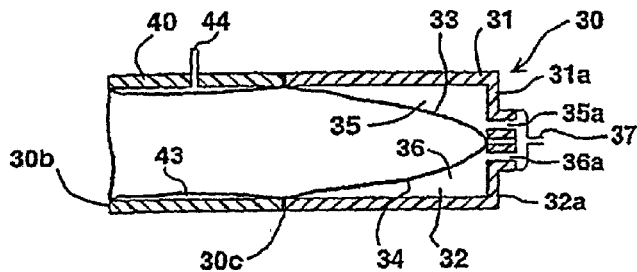

Signed and Sealed this

Twelfth Day of November, 2002

Attest:

JAMES E. ROGAN
Attesting Officer    Director of the United States Patent and Trademark Office